United States Patent
Cullen et al.

(10) Patent No.: US 11,602,733 B2
(45) Date of Patent: Mar. 14, 2023

(54) CATALYST AND A PROCESS FOR THE PRODUCTION OF ETHYLENICALLY UNSATURATED CARBOXYLIC ACIDS OR ESTERS

(71) Applicant: MITSUBISHI CHEMICAL UK LIMITED, Billingham (GB)

(72) Inventors: Adam Cullen, Redcar (GB); David William Johnson, Redcar (GB); Ian Andrew York, Redcar (GB)

(73) Assignee: MITSUBISHI CHEMICAL UK LIMITED, Billingham (GB)

( * ) Notice: Subject to any disclaimer, the term of this patent is extended or adjusted under 35 U.S.C. 154(b) by 77 days.

(21) Appl. No.: 16/646,763

(22) PCT Filed: Sep. 13, 2018

(86) PCT No.: PCT/GB2018/052606
§ 371 (c)(1),
(2) Date: Mar. 12, 2020

(87) PCT Pub. No.: WO2019/053438
PCT Pub. Date: Mar. 21, 2019

(65) Prior Publication Data
US 2020/0269214 A1 Aug. 27, 2020

(30) Foreign Application Priority Data
Sep. 13, 2017 (GB) .................................... 1714756

(51) Int. Cl.
*B01J 21/08* (2006.01)
*B01J 23/04* (2006.01)
(Continued)

(52) U.S. Cl.
CPC ............... *B01J 21/08* (2013.01); *B01J 23/04* (2013.01); *B01J 35/02* (2013.01); *B01J 37/0207* (2013.01);
(Continued)

(58) Field of Classification Search
CPC . B01J 21/066; B01J 21/08; B01J 23/04; B01J 35/02; B01J 37/0207; C07C 51/353; C07C 67/313
(Continued)

(56) References Cited

U.S. PATENT DOCUMENTS

| 3,933,888 A | 1/1976 | Schlaefer |
| 4,308,172 A | 12/1981 | McDaniel |

(Continued)

FOREIGN PATENT DOCUMENTS

| CN | 1558794 A | 12/2004 |
| EP | 0775164 B1 | 11/2001 |

(Continued)

OTHER PUBLICATIONS

Monros, G. et al., 1993, Journal of Materials Science, 28, 5852-5862.*

(Continued)

*Primary Examiner* — Brian A McCaig
(74) *Attorney, Agent, or Firm* — Shumaker, Loop & Kendrick, LLP

(57) ABSTRACT

A catalyst has a modified silica support and comprises a modifier metal, zirconium and/or hafnium, and a catalytic metal on the modified support. The catalyst has at least a proportion, typically, at least 25%, of modifier metal present in moieties having a total of up to 2 modifier metal atoms. The moieties may be derived from a monomeric and/or dimeric cation source. A method of production:—

(Continued)

HRTEM images of Example 5 (monomeric Zr).

provides a silica support with isolated silanol groups with optional treatment to provide isolated silanol groups (—SiOH) at a level of <2.5 groups per nm$^2$;

contacting the optionally treated silica support with a monomeric zirconium or hafnium modifier metal compound to effect adsorption onto the support;

optionally calcining the modified support for a time and temperature sufficient to convert the monomeric zirconium or hafnium compound adsorbed on the surface to an oxide or hydroxide of zirconium or hafnium in preparation for catalyst impregnation.

13 Claims, 5 Drawing Sheets

(51) Int. Cl.
  *B01J 35/02* (2006.01)
  *B01J 37/02* (2006.01)
  *B01J 21/06* (2006.01)
  *C07C 51/353* (2006.01)
  *C07C 67/313* (2006.01)

(52) U.S. Cl.
  CPC .......... *B01J 21/066* (2013.01); *C07C 51/353* (2013.01); *C07C 67/313* (2013.01)

(58) Field of Classification Search
  USPC ........................................................ 502/237
  See application file for complete search history.

(56) References Cited

U.S. PATENT DOCUMENTS

| | | | |
|---|---|---|---|
| 4,357,451 A | | 11/1982 | McDaniel |
| 4,412,914 A | * | 11/1983 | Hettinger, Jr. .......... C10G 25/06 208/253 |
| 5,069,816 A | | 12/1991 | DeSantis et al. |
| 5,583,085 A | | 12/1996 | Ward |
| 5,861,352 A | | 1/1999 | Gila et al. |
| 5,972,823 A | | 10/1999 | Walzer, Jr. |
| 6,544,924 B1 | | 4/2003 | Jackson et al. |
| 8,940,924 B2 | | 1/2015 | Johnson et al. |
| 2003/0069130 A1 | * | 4/2003 | Hu ............................ B01J 23/04 502/234 |
| 2014/0045953 A1 | * | 2/2014 | Daly .................... B01J 37/0213 502/241 |

FOREIGN PATENT DOCUMENTS

| | | |
|---|---|---|
| EP | 1233330 A2 | 8/2002 |
| EP | 1429865 B1 | 3/2006 |
| JP | S49-070919 A | 7/1974 |
| JP | H10-503798 A | 4/1998 |
| JP | 2002-511336 A | 4/2002 |
| JP | 2005-503913 A | 2/2005 |
| JP | 2015-533846 A | 11/2015 |
| RU | 2203731 C2 | 5/2003 |
| RU | 2579516 C2 | 4/2016 |
| WO | 9952628 A1 | 10/1999 |
| WO | 1999052628 A1 | 10/1999 |
| WO | 03026795 A1 | 4/2003 |
| WO | 2007005676 A2 | 1/2007 |
| WO | 2009003722 A1 | 1/2009 |
| WO | 2013022095 A1 | 2/2013 |
| WO | 2019053438 A1 | 3/2019 |

OTHER PUBLICATIONS

International Search Report for International application No. PCT/GB2018/052606; dated Jan. 15, 2019; 29 pages.

Sulym, I.Y. et al.; "Structural and hydrophobic-hydrophilic properties of nanosilica/zirconia along and with adsorbed PDMS,"; Applied Surface Science, Elsevier, Amsterdam, NL, vol. 258, No. 1, dated Aug. 9, 2011; pp. 270-277.

Arnaldo C. Faro et al.; "Zirconia-alumina mixing in alumina-supported zirconia prepared by impregnation with solutions of zirconium acetylacetonate", Physical Chemistry Chemical Physis, vol. 5, No. 9; dated Apr. 16, 2003 pp. 1932-1940.

Legrand, Andre P.; Laboratoire de Physique Quantique, ESPCI, Paris, France; "The surface properties of silicas", John Wiley & Sons Inc., 1998, (ISBN 047195332-6); pp. 147-234.

Busto, Mariana, et al., "Silica supported tungsta-zirconia catalysts for hydroisomerization-cracking of long alkanes," Applied Catalysis A: General 355 (2009) 123-131, 2008.

Hu, Yung-Jin, et al., "Understanding the Role of Aqueous Solution Speciation and Its Application to the Directed Syntheses of Complex Oxidic Zr Chlorides and Sulfates," J. Am. Chem. Soc. 2013, 135, 38, 14240-14248, Aug. 22, 2013, https://doi.org/10.1021/ja405555h.

Bosman, H.J.M , et al., "Characterization of the Acid Strength of SiO2—ZrO2 Mixed Oxides," Journal of Catalysis, vol. 148, Issue 2, Aug. 1994, pp. 660-672, https://doi.org/10.1006/jcat.1994.1253.

Zhuravlev, L.T., "The surface chemistry of amorphous silica. Zhuravlev model," Colloids and Surfaces A: Physicochemical and Engineering Aspects, vol. 173, Issues 1-3, Nov. 10, 2000, pp. 1-38, https://doi.org/10.1016/S0927-7757(00)00556-2.

Iler, Ralph K., "The Chemistry of Silica: Solubility, Polymerization, Colloid and Surface Properties and Biochemistry of Silica," John Wiley & Sons Inc., Jun. 1979, pp. 358-364.

Monros, G., et al., "Effect of hydrolysis time and type of catalyst on the stability of tetragonal zirconia-silica composites synthesized from alkoxides," Journal of Material Science 28, 5852-5862 (1993), https://doi.org/10.1007/BF00365192.

English translation of Russian Office Action for Russian Patent Application 2020113238 dated Oct. 28, 2021 (10 pages).

English translation of Russian Search Report for Patent Application 2020113238 dated Oct. 28, 2021 (2 pages).

Translation of Corma et al. (WO 2013/022095), published Feb. 2013, 14 pp.

Non-Final Office Action issued for U.S. Appl. No. 17/181,444 dated Sep. 15, 2022 (14 pages).

Japanese Office Action issued for JP Patent Application No. 2020-514951 dated Jul. 12, 2022 with English Translation (17 pages).

Chinese Office Action for CN App. No. 1558794 dated Dec. 21, 2022 (14 pages).

\* cited by examiner

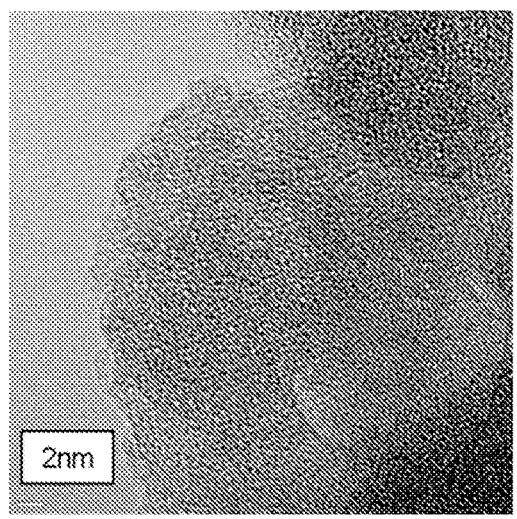
Figure 1: HRTEM images of Example 5 (monomeric Zr).
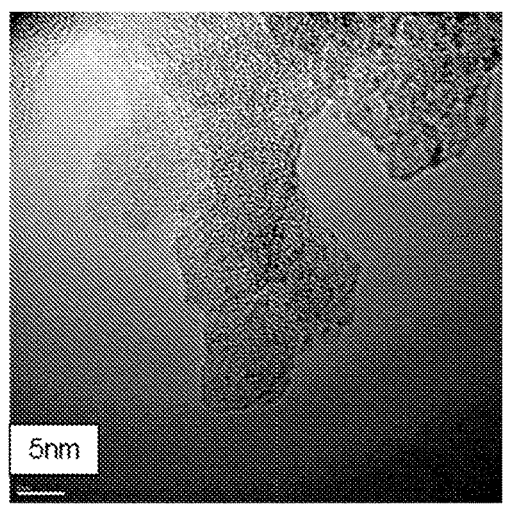
Figure 2: HRTEM images of Example 7 (monomeric Zr).
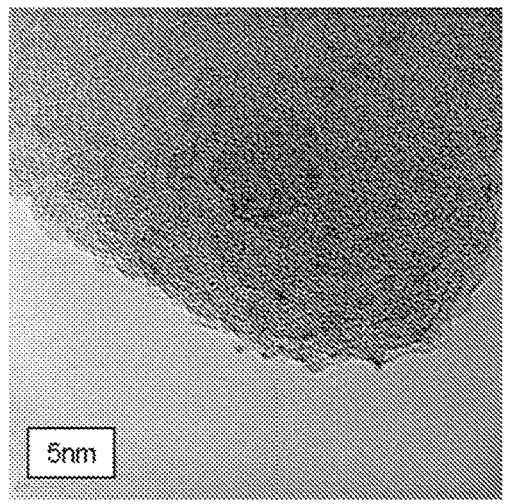
Figure 3: HRTEM images of Example 14 (trimeric Zr).

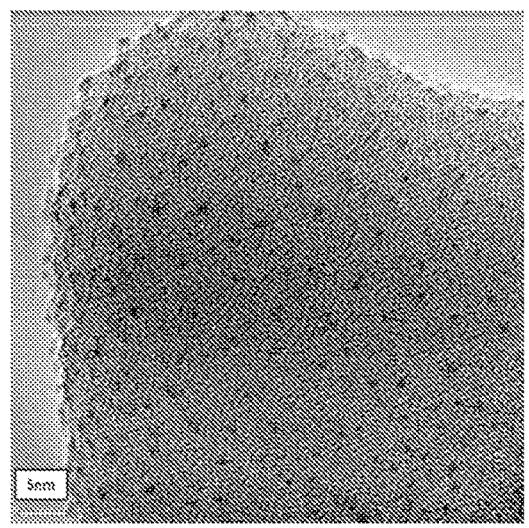
Figure 4: HRTEM images of Example 15 (pentameric Zr).
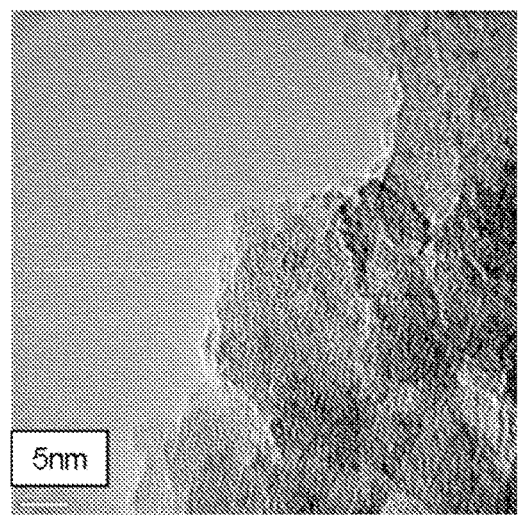
Figure 5 HRTEM images of Example 17 (monomeric Hf).
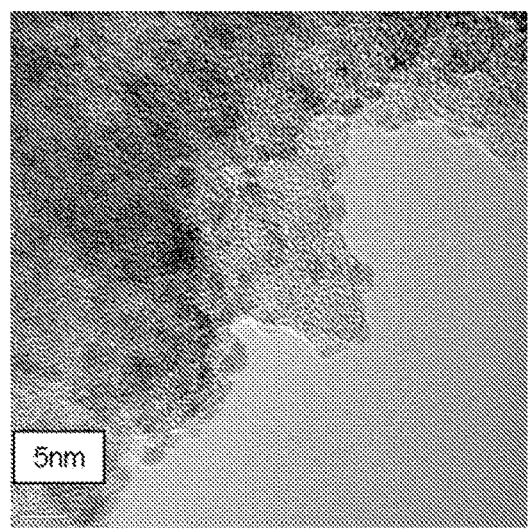
Figure 6: HRTEM images of Example 18 (trimeric Hf).

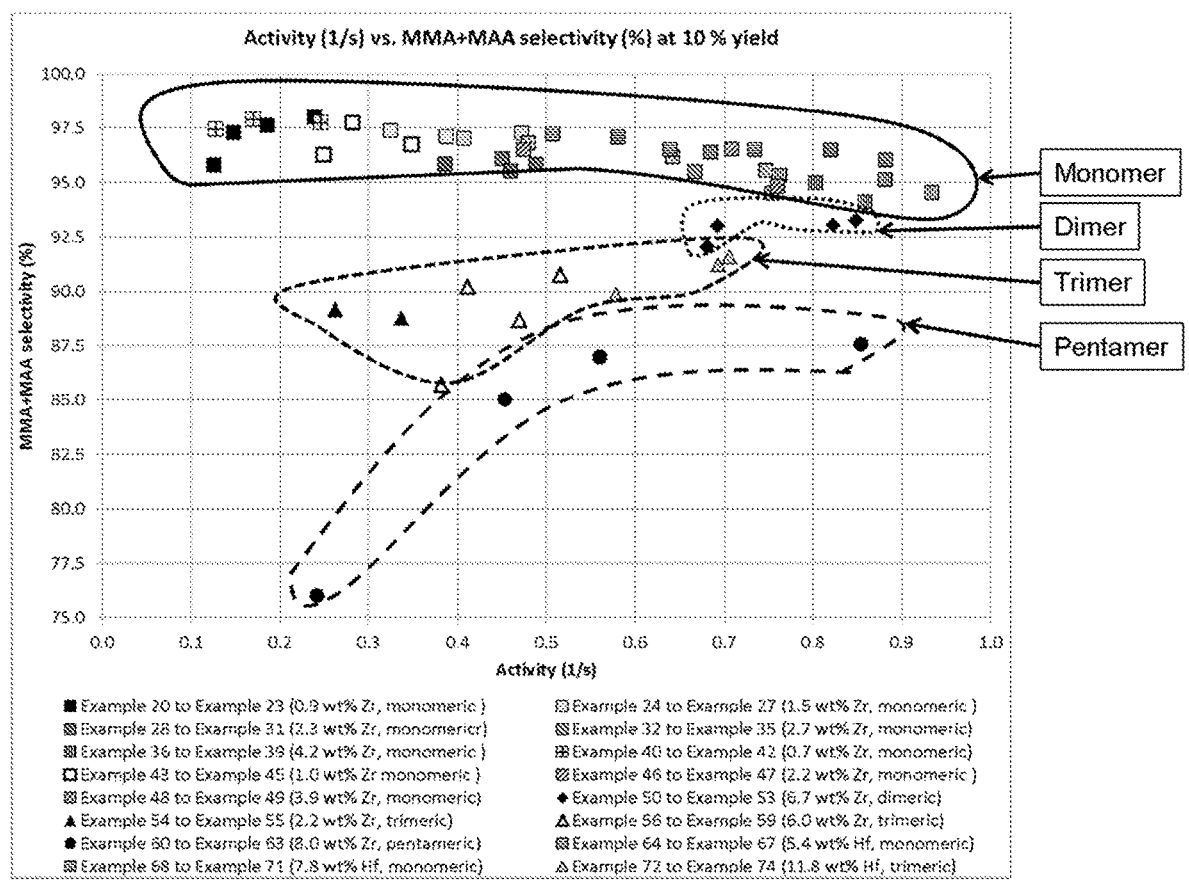
Figure 7: MMA+MAA selectivity (%) vs. Activity (1/s) at 10% yield for the catalysts described in Example 20 to Example 74.

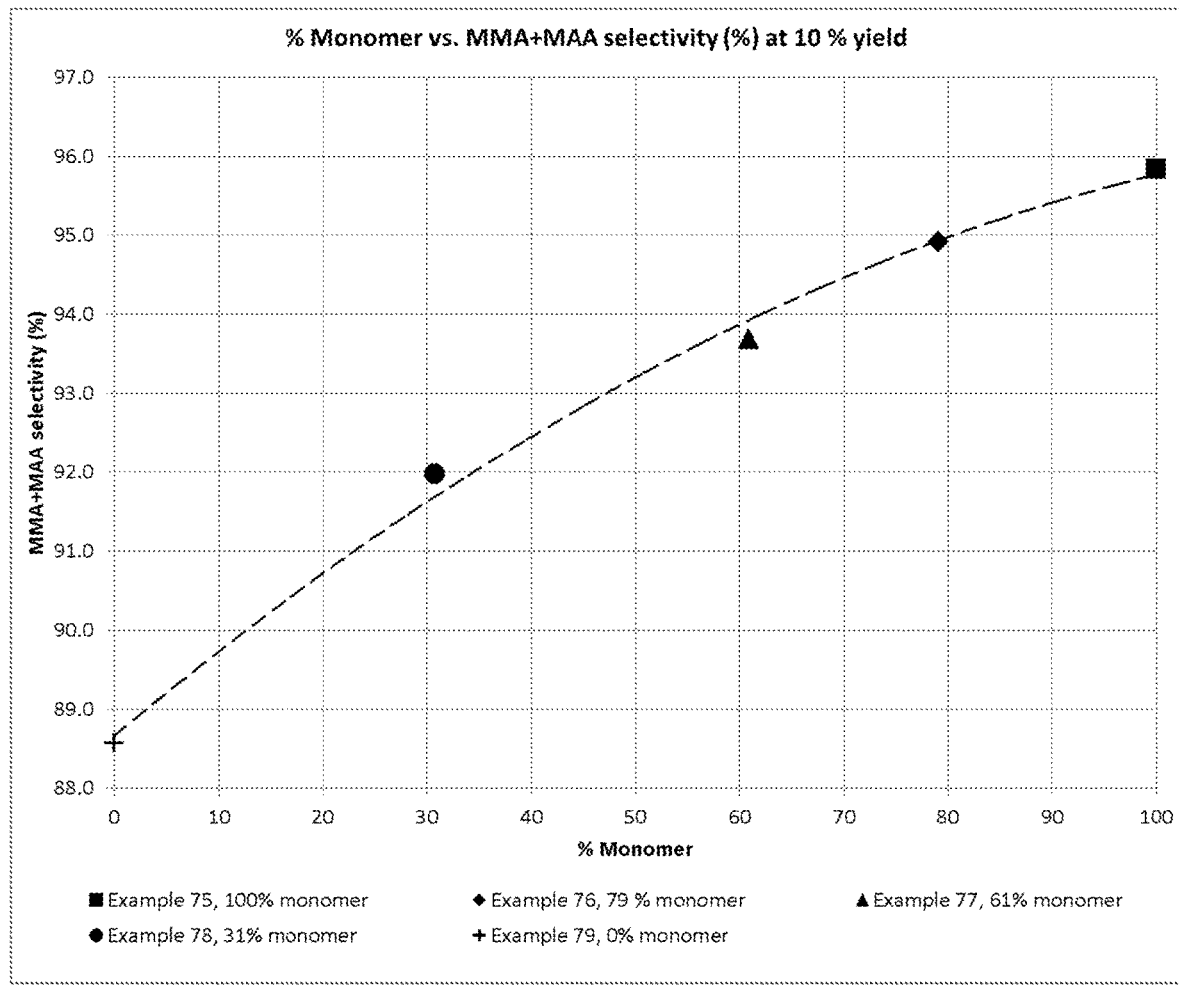
Figure 8: MMA+MAA selectivity (%) vs monomer content (%) based on Zr content for Example 75 to Example 79.

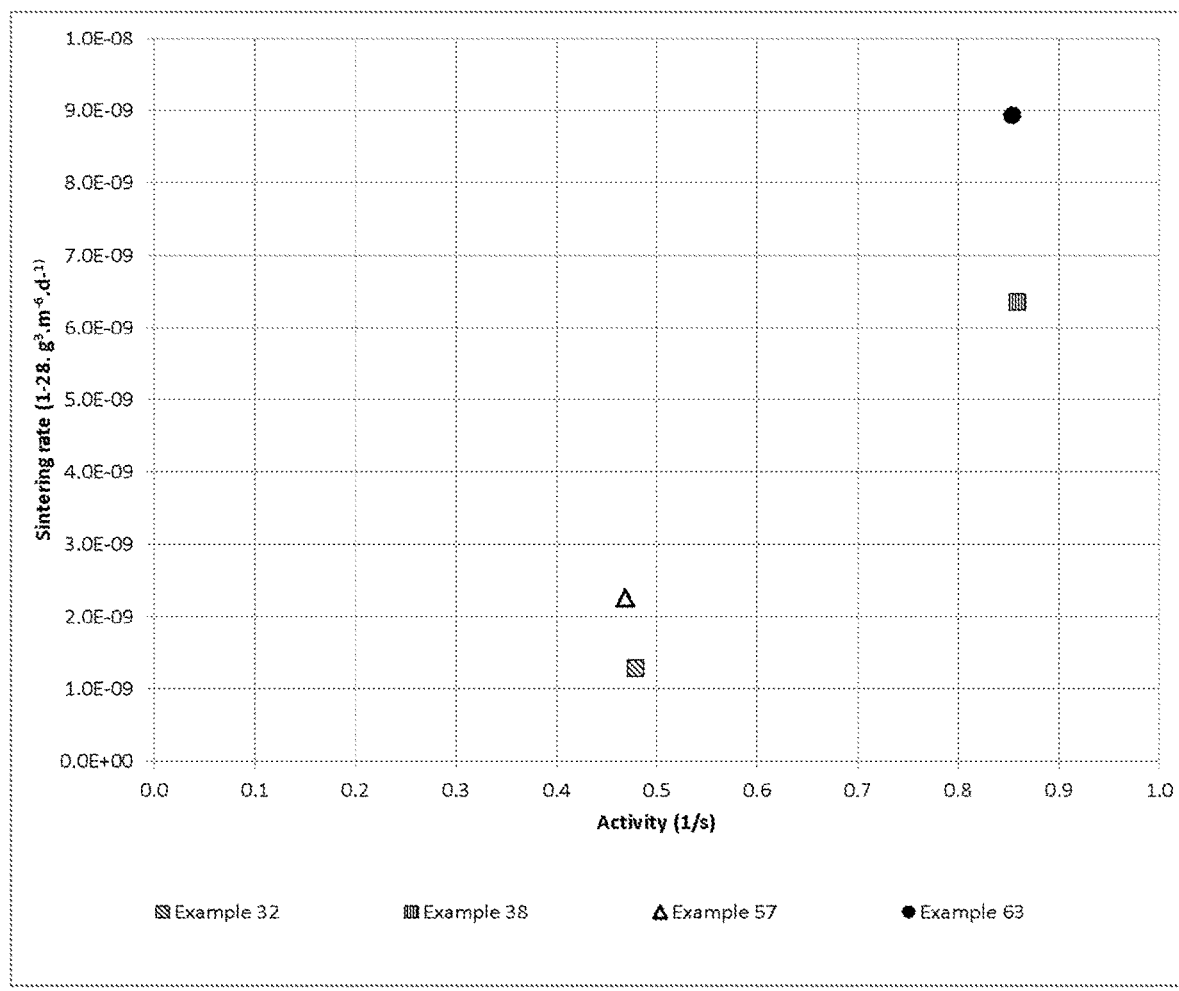
Figure 9: Sintering rate ($g^3.m^{-6}.d^{-1}$) vs. catalyst activity (1/s) for monomeric, trimeric and pentameric Zr catalysts.

CATALYST AND A PROCESS FOR THE PRODUCTION OF ETHYLENICALLY UNSATURATED CARBOXYLIC ACIDS OR ESTERS

CROSS REFERENCE TO RELATED PATENT APPLICATIONS

This application claims the benefit of and priority to PCT/GB2018/052606 filed Sep. 13, 2018 which claims the benefit of and priority to Great Britain Application No. 1714756.2 filed on Sep. 13, 2017.

TECHNICAL FIELD AND BACKGROUND OF THE INVENTION

The present invention relates to a modified silica catalyst support, a catalyst incorporating the modified silica support and a process for the production of ethylenically unsaturated carboxylic acids or esters, particularly α, β unsaturated carboxylic acids or esters, more particularly acrylic acids or esters such as (alk)acrylic acids or alkyl (alk)acrylates particularly (meth)acrylic acids or alkyl (meth)acrylates such as methacrylic acid (MA) and methyl methacrylate (MMA) by the condensation of carboxylic acid or esters with formaldehyde or a source thereof such as dimethoxymethane in the presence of such catalysts, in particular, by the condensation of propionic acid or alkyl esters thereof such as methyl propionate with formaldehyde or a source thereof in the presence of such modified silica supported catalytic metal catalysts. The invention is therefore particularly relevant to the production of methacrylic acid (MAA) and methyl methacrylate (MMA).

As mentioned above, such unsaturated acids or esters may be made by the reaction of a carboxylic acid or ester and suitable carboxylic acids or esters are alkanoic acids (or esters) of the formula $R^3$—$CH_2$—$COOR^4$, where $R^3$ and $R^4$ are each, independently, a suitable substituent known in the art of acrylic compounds such as hydrogen or an alkyl group, especially a lower alkyl group containing, for example, 1-4 carbon atoms. Thus, for instance, methacrylic acid or alkyl esters thereof, especially methyl methacrylate, may be made by the catalytic reaction of propionic acid, or the corresponding alkyl ester, e.g. methyl propionate, with formaldehyde as a methylene source in accordance with the reaction sequence 1.

and

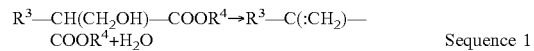    Sequence 1

An example of reaction sequence 1 is reaction sequence 2

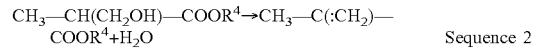    Sequence 2

The above reaction sequences are typically effected at an elevated temperature, usually in the range 250-400° C., using and acid/base catalyst. Where the desired product is an ester, the reaction is typically effected in the presence of the relevant alcohol in order to minimise the formation of the corresponding acid through hydrolysis of the ester. Also for convenience it is often desirable to introduce the formaldehyde in the form of a complex of formaldehyde with methanol. Hence, for the production of methyl methacrylate, the reaction mixture fed to the catalyst will generally consist of methyl propionate, methanol, formaldehyde and water.

A known production method for MMA is the catalytic conversion of methyl propionate (MEP) to MMA using formaldehyde. A known catalyst for this is a caesium catalyst incorporating a support, for instance, silica.

WO1999/52628 discloses a catalyst for use in the production of α, β unsaturated carboxylic acids or esters by the condensation of propionic acid or the corresponding alkyl ester wherein the catalyst comprises alkali metal doped silica impregnated with at least one modifier element wherein the modifier element is selected from a group consisting of boron, aluminium, magnesium, zirconium and hafnium, preferably zirconium and/or aluminium and/or boron and the alkali metal is selected from potassium, rubidium or caesium, preferably caesium.

WO2003/026795 discloses a catalyst for use in aldol condensations including the production of α, β unsaturated carboxylic acids by the condensation of propionic acid or propionic ester, olefin polymerisation, dehydration, hydroxylation and isomerisation wherein the catalyst comprises a silica-metal hydrogel impregnated with a catalytic metal wherein the metal of the hydrogel is selected from a group consisting of zirconium, titanium, aluminium and iron, preferably zirconium, and the catalytic metal is selected from a group consisting of alkali metals and alkaline earth metals, preferably caesium.

The present inventors have now discovered that catalysts comprising certain metal modified silica supports, and containing a catalytic metal, provide a high level of selectivity in the condensation of methylene sources such as formaldehyde with a carboxylic acid or alkyl ester such as methyl propionate when at least a proportion of the modifier metal is incorporated or present in the support in the form of metal species having a total of up to two zirconium and/or hafnium atoms.

It is known from Yung-Jin Hu et al, J. Am. Chem. Soc. Volume 135, 2013, p 14240, that zirconium is capable of forming large clusters in solution. Zr-18 clusters are typical.

However, the current inventors have surprisingly found that when the modified silica support comprises zirconium and/or hafnium oxide moieties derived from a monomeric and/or dimeric modifier metal cation source such as a compound thereof at the commencement of the modification, rather than such larger clusters, there has been found to be an improvement in catalytic metal binding to the modified support and thereafter higher selectivity for the production of unsaturated carboxylic acid or esters by condensation of the corresponding acid or ester with a methylene source such as formaldehyde. Furthermore, the inventors have found that the modified silica supports providing these high selectivities contain monomeric or dimeric modifier metal atoms after deposition/adsorption onto the surface of the silica.

Still further, the present inventors have found that when such modified silica supports are used, the rate of catalyst surface sintering has been found to be retarded and loss of surface area upon which the catalytic reaction takes place during the condensation reaction is reduced.

Therefore, catalysts comprising such modified silica supports and containing a catalytic metal are remarkably effective catalysts for the production of α, β ethylenically unsaturated carboxylic acids or esters by condensation of the corresponding acid or ester with a methylene source such as formaldehyde providing several advantages such as high levels of selectivity and/or reduced sintering of the catalyst surface.

BRIEF SUMMARY OF THE INVENTION

Therefore, according to a first aspect of the present invention, there is provided a catalyst comprising
a modified silica support,
the modified silica support comprising a modifier metal;
and a catalytic metal on the modified silica support,
wherein the modifier metal is selected from one or more of zirconium and/or hafnium,
characterised in that at least a proportion, typically, at least 25%, of the said modifier metal is present in the form of modifier metal moieties
having a total of up to 2 modifier metal atoms.

According to a further aspect of the present invention, there is provided a catalyst comprising
a modified silica support,
the modified silica support comprising a modifier metal;
and a catalytic metal on the modified silica support,
wherein the modifier metal is selected from one or more of zirconium and/or hafnium,
characterised in that at least a proportion, typically, at least 25%, of the said modifier metal is present in the form of modifier metal moieties derived from a monomeric and/or dimeric modifier metal cation source.

The monomeric and/or dimeric modifier metal contacts the silica support as a monomeric and/or dimeric zirconium or hafnium modifier metal cation source such as a compound thereof in solution to effect adsorption of the said modifier metal onto the support to thereby form the modifier metal moieties. A suitable source may be a complex of the modifier metal, more typically, a ligand complex in solution.

According to a second aspect of the present invention, there is provided a modified silica support for a catalyst comprising
a silica support and
a modifier metal
wherein the modifier metal is selected from one or more of zirconium and/or hafnium,
characterised in that at least a proportion, typically, at least 25%, of the said modifier metal is present in the form of modifier metal moieties
having a total of up to 2 modifier metal atoms.

According to a third aspect of the present invention, there is provided a modified silica support for a catalyst comprising
a silica support and
a modifier metal
wherein the modifier metal is selected from one or more of zirconium and/or hafnium
characterised in that at least a proportion, typically, at least 25%, of the said modifier metal is present in the form of modifier metal moieties derived from a monomeric and/or dimeric modifier metal cation source at the commencement of the modification.

The modified silica support herein is modified by the modifier metal. Typically, the modifier metal is an adsorbate adsorbed on the silica support surface. The adsorbate may be chemisorbed or physisorbed onto the silica support surface, typically, it is chemisorbed thereon. The modifier metal moieties are generally modifier metal oxide moieties.

The silica support is generally in the form of a silica gel, more typically, a xerogel or a hydrogel Typically, the modifier metal is adsorbed on the silica gel support surface. Therefore, typically, said modifier metal is present on the modified silica gel support surface in the form of metal oxide moieties.

Alternatively, the modifier metal may be present in the support in the form of a co-gel. In such a case the modified silica support is a silica-metal oxide gel, typically, comprising zirconium and/or hafnium oxide moieties.

Typically, the modifier metal is present in the modified silica support in an effective amount to reduce sintering and improve selectivity of the catalyst. Typically, at least 30%, such as at least 35%, more preferably at least 40%, such as at least 45%, most suitably at least 50%, such as at least 55%, for example at least 60% or 65%, and most preferably at least 70% such as at least 75% or 80%, more typically, at least 85%, most typically, at least 90%, especially, at least 95% of the modifier metal in the modified silica support is in moieties having a total of 1 and/or 2 metal atoms, especially, in moieties having a total of 1 metal atom or is derived from a monomeric and/or dimeric metal compound at the commencement of the modified silica formation at such levels.

For the avoidance of doubt, modifier metal moieties having a total of 1 metal atom are considered monomeric and having a total of 2 metal atoms are dimeric. In particularly preferred embodiments, such as at least 35%, more preferably at least 40%, such as at least 45%, most suitably at least 50%, such as at least 55%, for example at least 60% or 65%, and most preferably at least 70% such as at least 75% or 80%, more typically, at least 85%, most typically, at least 90%, especially, at least 95% of the modifier metal is present in monomeric metal moieties, or, in any case, is typically derived from zirconium and/or hafnium compounds at the commencement of the modification having such levels of modifier metal as monomeric compounds. Generally, the modifier metal moieties on the silica are modifier metal oxide moieties.

Clusters of zirconium and/or hafnium larger than 2 metal atoms dispersed throughout the support such as a hydrogel support, have surprisingly been found to decrease reaction selectivity for the production of α, β ethylenically unsaturated carboxylic acids or esters by condensation of the corresponding acid or ester with a methylene source such as formaldehyde. Such large clusters have also surprisingly been found to increase sintering of the modified silica particles relative to clusters of modifier metal with 2 or 1 metal atom(s) thereby reducing the surface area which lowers strength and reduces the life of the catalyst before activity becomes unacceptably low. In addition, selectivity is often lower, depending on the nature of the cluster of the modifier metal.

Typically, the modifier metal is dispersed throughout the support in a substantially homogeneous manner.

Typically, the modified silica support is a xerogel. The gel may also be a hydrogel or an aerogel.

The gel may also be a silica-zirconia and or silica-hafnia co-gel. The silica gel may be formed by any of the various techniques known to those skilled in the art of gel formation such as mentioned herein. Typically, the modified silica gels are produced by a suitable adsorption reaction. Adsorption of the relevant metal compounds such as zirconium and/or hafnium compounds to a silica gel such as a silica xerogel to form modified silica gel having the relevant modifier metal moieties is a suitable technique.

Methods for preparing silica gels are well known in the art and some such methods are described in The Chemistry of Silica: Solubility, Polymerisation, Colloid and Surface Properties and Biochemistry of Silica, by Ralph K Iler, 1979, John Wiley and Sons Inc., ISBN 0-471-02404-X and references therein.

Methods for preparing silica-zirconia co-gels are known in the art and some such methods are described in U.S. Pat. No. 5,069,816, by Bosman et al in J Catalysis Vol. 148 (1994) page 660 and by Monros et al in J Materials Science Vol. 28, (1993), page 5832.

In preferred embodiments, the modified silica support is not formed by co-gelation i.e. not a silica-zirconia, silica-hafnia or silica-zirconia/hafnia formed by co-gelation such as by mixing of sodium silicate solution with modifier metal complexes in sulphuric acid solution. In such embodiments, the zirconium and/or hafnium is typically incorporated as an adsorbate on the silica support surface.

Preferably, the modified silica supported catalyst and modified silica support according to any aspect of the present invention may be substantially free, may be essentially free or may be completely free of fluoride. Fluoride may be present in trace amounts because of unavoidable contamination from the environment. By "substantially free" we mean to refer to catalysts and supports containing less than 1000 parts per million (ppm) of fluoride. By "essentially free" we mean to refer to catalysts and supports containing less than about 100 ppm of fluoride and by "completely free" we mean to refer to catalysts containing less than 200 parts per billion (ppb) of fluoride.

Advantageously, when at least a proportion of the modifier metal incorporated into the modified silica of the above aspects of the present invention is derived from a monomeric and/or dimeric modifier metal cation source at the commencement of the modified silica formation, there has been found to be improved reaction selectivity and/or reduced rate of sintering of the catalyst surface during the production of α, β ethylenically unsaturated carboxylic acids or esters.

Metal and metal oxide moieties in the modified silica support according to the present invention relate to zirconium and/or hafnium and zirconia and/or hafnia, not to silica.

Preferably, the level of modifier metal present in the modified silica or catalyst may be up to $7.6 \times 10^{-2}$ mol/mol of silica, more preferably up to $5.9 \times 10^{-2}$ mol/mol of silica, most preferably up to $3.5 \times 10^{-2}$ mol/mol of silica. Typically, the level of such metal is between $0.067 \times 10^{-2}$ and $7.3 \times 10^{-2}$ mol/mol of silica, more preferably, between $0.13 \times 10^{-2}$ and $5.7 \times 10^{-2}$ mol/mol of silica and most preferably between $0.2 \times 10^{-2}$ and $3.5 \times 10^{-2}$ mol/mol of silica. Typically, the level of modifier metal present is at least $0.1 \times 10^{-2}$ mol/mol of silica, more preferably, at least $0.15 \times 10^{-2}$ mol/mol of silica and most preferably at least $0.25 \times 10^{-2}$ mol/mol of silica.

Preferably, when zirconium is the modifier metal, the level of zirconium metal may be up to 10% w/w of the modified silica support, more preferably up to 8% w/w, most preferably up to 5.5% w/w. Typically, the level of zirconium metal is between 0.1-10% w/w of the modified silica support, more preferably between 0.2-8% w/w and most preferably between 0.3-5% w/w. Typically, the level of zirconium metal is at least 0.5% w/w of the modified silica support, such as 0.8% w/w, more typically, at least 1.0% w/w, most typically, at least 1.5% w/w.

Preferably, the level of hafnium metal may be up to 20% w/w of the modified silica support, more preferably up to 16% w/w, most preferably up to 10% w/w. Typically, the level of hafnium metal is between 0.2-20% w/w of the modified silica support, more preferably between 0.4-16% w/w and most preferably between 0.6-10% w/w. Typically, the level of hafnium metal is at least 1.0% w/w of the modified silica support, more typically, 2.0% w/w, most typically, at least 3.0% w/w.

The silica component of the silica-zirconium oxide support may typically form 86.5-99.9 wt % of the modified support, more typically 89.2-99.7 wt %, most typically 93.2-99.6 wt % thereof.

The silica component of the silica-hafnium oxide support typically forms 76.4-99.8 wt % of the modified support, more typically 81.1-99.5 wt %, most typically 88.2-99.3 wt % thereof.

By the term "up to 2 metal atoms" or the like as used herein, is meant 1 and/or 2 metal atoms. Preferably, the modified silica support and catalyst according to any aspects of the present invention comprise metal moieties, typically, metal oxide moieties having up to 2 metal atoms and most preferably, 1 metal atom. Accordingly, it will be appreciated that such moieties are monomeric, or dimeric metal moieties.

Preferably, the catalytic metal may be one or more alkali metals. The catalytic metal is a metal other than zirconium or hafnium. Suitable alkali metals may be selected from potassium, rubidium and caesium, suitably rubidium and caesium. Caesium is the most preferred catalytic metal.

Suitably the catalytic metals such as caesium may be present in the catalyst at a level of at least 1 mol/100 (silicon+metal (zirconium and/or hafnium)) mol more preferably, at least 1.5 mol/100 (silicon+metal) mol, most preferably, at least 2 mol/100 (silicon+metal) mol. The level of catalytic metal may be up to 10 mol/100 (silicon+metal) mol in the catalyst, more preferably, up to 7.5 mol/100 (silicon+metal) mol, most preferably, up to 5 mol/100 (silicon+metal) mol in the catalyst.

Preferably, the level of catalytic metal in the catalyst is in the range from 1-10 mol/100 (silicon+metal) mol, more preferably, 2-8 mol/100 (silicon+metal) mol, most preferably, 2.5-6 mol/100 (silicon+metal) mol in the catalyst.

Unless indicated to the contrary, amounts of alkali metal or alkali metal in the catalyst relate to the alkali metal ion and not the salt.

Alternatively, the catalyst may have a wt % of catalytic metal in the range 1 to 22 wt % in the catalyst, more preferably 4 to 18 wt %, most preferably, 5-13 wt %. These amounts would apply to all alkali metals, but especially caesium.

The catalyst may comprise any suitable weight ratio of catalytic alkali metal:zirconium and/or hafnium metal. However, typically, the weight ratios for caesium:zirconium are in the range from 2:1 to 10:1, more preferably from 2.5:1 to 9:1, most preferably from 3:1 to 8:1 in the catalyst, for caesium:hafnium are in the range from 1:1 to 5:1, more preferably from 1.25:1 to 4.5:1, most preferably from 1.5:1 to 4:1 in the catalyst, for rubidium:zirconium are in the range from 1.2:1 to 8:1, more preferably from 1.5:1 to 6:1, most preferably from 2:1 to 5:1 in the catalyst, for rubidium:hafnium are in the range from 0.6:1 to 4:1, more preferably from 0.75:1 to 3:1, most preferably from 1:1 to 2.5:1 in the catalyst. Accordingly, the catalytic metal:modifier metal mole ratio in the catalyst is typically at least 1.4 or 1.5:1, preferably, it is in the range 1.4 to 2.7:1 such as 1.5 to 2.1:1, especially, 1.5 to 2.0 to :1, typically in this regard the modifier metal is zirconium and the catalytic metal is caesium. Generally, herein, the catalytic metal is in excess of that which would be required to neutralise the modifier metal.

Preferably, the catalytic metal is present in the range 0.5-7.0 mol/mol modifier metal, more preferably 1.0-6.0 mol/mol, most preferably 1.5-5.0 mol/mol modifier metal.

Suitably, the catalytic metal may be incorporated into the modified silica support by any method known in the art such as impregnation, co-gelation or vapour deposition with the catalytic metal.

By the term "impregnated" as used herein is included the addition of the catalytic metal dissolved in a solvent, to make a solution, which is added to the xerogel or aerogel, such that the solution is taken up into the voidages within the said xerogel or aerogel.

Typically, the catalyst of the invention may be in any suitable form. Typical embodiments are in the form of discrete particles. Typically, in use, the catalyst is in the form of a fixed bed of catalyst. Alternatively, the catalyst may be in the form of a fluidised bed of catalyst. A further alternative is a monolith reactor.

Where the catalysts are used in the form of a fixed bed, it is desirable that the supported catalyst is formed into granules, aggregates or shaped units, e.g. spheres, cylinders, rings, saddles, stars, poly-lobes prepared by pelleting, or extrusion, typically having maximum and minimum dimensions in the range 1 to 10 mm, more preferably, with a mean dimension of greater than 2 mm such as greater than 2.5 or 3 mm. The catalysts are also effective in other forms, e.g. powders or small beads of the same dimensions as indicated. Where the catalysts are used in the form of a fluidised bed it is desirable that the catalyst particles have a maximum and minimum dimension in the range of 10-500 µm, preferably 20-200 µm, most preferably 20-100 µm.

Levels of catalytic metal in the catalyst whether atoms/100 atoms (silicon+zirconium and/or hafnium) or wt % may be determined by appropriate sampling and taking an average of such samples. Typically, 5-10 samples of a particular catalyst batch would be taken and alkali metal levels determined and averaged, for example by XRF, atomic absorption spectroscopy, neutron activation analysis, ion coupled plasma mass spectrometry (ICPMS) analysis or ion coupled plasma atomic emission spectroscope (ICPAES).

Levels of the metal oxide of particular types in the catalyst/support are determined by XRF, atomic absorption spectroscopy, neutron activation analysis or ion coupled plasma mass spectrometry (ICPMS) analysis.

The typical average surface area of the modified silica supported catalyst according to any aspect of the invention is in the range 20-600 $m^2/g$, more preferably 30-450 $m^2/g$ and most preferably 35-350 $m^2/g$ as measured by the B.E.T. multipoint method using a Micromeritics Tristar 3000 Surface Area and porosity analyser. The reference material used for checking the instrument performance may be a carbon black powder supplied by Micromeritics with a surface area of 30.6 $m^2/g$ (+/−0.75 $m^2/g$), part number 004-16833-00.)

If the catalyst material is porous, it is typically a combination of mesoporous and macroporous with an average pore size of between 2 and 1000 nm, more preferably between 3 and 500 nm, most preferably between 5 and 250 nm. Macropore size (above 50 nm) can be determined by mercury intrusion porosimetry using NIST standards whilst the Barrett-Joyner-Halenda (BJH) analysis method using liquid nitrogen at 77K is used to determine the pore size of mesopores (2-50 nm). The average pore size is the pore volume weighted average of the pore volume vs. pore size distribution.

The average pore volume of the catalyst particles may be less than 0.1 $cm^3/g$ but is generally in the range 0.1-5 $cm^3/g$ as measured by uptake of a fluid such as water. However, microporous catalysts with very low porosity are not the most preferred because they may inhibit movement of reagents through the catalyst and a more preferred average pore volume is between 0.2-2.0 $cm^3/g$. The pore volume can alternatively be measured by a combination of nitrogen adsorption at 77K and mercury porosimetry. The Micromeritics TriStar Surface Area and Porosity Analyser is used to determine pore volume as in the case of surface area measurements and the same standards are employed.

In the present invention, it has been found that controlling the size of the modifier metal moieties is surprisingly advantageous. However, to obtain the greatest benefit it is necessary to control the proximity of neighbouring modifier metal moieties because the modifier metal moieties may otherwise combine with each other and thus increase the size of the modifier metal moiety.

Therefore, according to a fourth aspect of the present invention, there is provided a method of producing a modified silica support comprising the steps of:

providing a silica support having silanol groups;

contacting the silica support with a monomeric and/or dimeric modifier metal compound so that modifier metal is adsorbed onto the surface of the silica support through reaction with said silanol groups.

Typically, the modifier metals are selected from zirconium or hafnium.

Preferably, the adsorbed modifier metal cations are sufficiently spaced apart from each other to substantially prevent oligomerisation thereof, more preferably trimerisation thereof with neighbouring modifier metal cations.

Typically, at least 25%, more typically, at least 30%, such as at least 35%, more preferably at least 40%, such as at least 45%, most suitably at least 50%, such as at least 55%, for example at least 60% or 65%, and most preferably at least 70% such as at least 75% or 80%, more typically, at least 85%, most typically, at least 90%, especially, at least 95% of the said modifier metals contacting the silica support in the contacting step are monomeric or dimeric modifier metals. Accordingly, at least 25%, more typically, at least 30%, such as at least 35%, more preferably at least 40%, such as at least 45%, most suitably at least 50%, such as at least 55%, for example at least 60% or 65%, and most preferably at least 70% such as at least 75% or 80%, more typically, at least 85%, most typically, at least 90%, especially, at least 95% of the modifier metals adsorbed onto the silica support are present in the form of modifier metal moieties having a total of up to 2 modifier metal atoms.

According to a further aspect of the present invention there is provided a method of producing a modified silica support according to any of the aspects herein comprising the steps of:

providing a silica support having silanol groups;

treating the silica support with monomeric and/or dimeric modifier metal compounds so that modifier metal is adsorbed onto the surface of the silica support through reaction with silanol groups, wherein the adsorbed modifier metal atoms are sufficiently spaced apart from each other to substantially prevent oligomerisation thereof with neighbouring modifier metal atoms, more preferably, sufficiently spaced apart from each other to substantially prevent trimerisation with neighbouring modifier metal atoms thereof.

Preferably, the spacing apart of the modifier metal atoms is effected by
 a) decreasing the concentration of silanol groups on the silica support and/or
 b) attaching a non-labile ligand of sufficient size to the modifier metal prior to treating the silica support.

According to a still further aspect there is provided a method of producing a catalyst comprising
the steps of:—
i. providing a silica support with isolated silanol groups and optionally treating the said support to provide isolated silanol groups (—SiOH) at a level of <2.5 groups per nm$^2$;
ii. contacting the optionally treated silica support with a monomeric zirconium or hafnium modifier metal compound to effect adsorption of the said modifier metal onto the support, typically to at least 25% of the said isolated silanol groups;
iii. optionally, removing any solvent or liquid carrier for the modifier metal compounds;
iv. calcining the modified silica for a time and temperature sufficient to convert the monomeric zirconium or hafnium compound adsorbed on the surface to an oxide or hydroxide of zirconium or hafnium;
v. treating the said calcined modified silica with a catalytic alkali metal to impregnate the modified silica with the catalytic metal to form the catalyst and optionally, calcining the catalyst.

According to an even further aspect of the present invention there is provided a method of producing a modified silica support for a catalyst comprising
the steps of:—
i. providing a silica support with isolated silanol groups and optionally treating the said support to provide isolated silanol groups (—SiOH) at a level of <2.5 groups per nm$^2$;
ii. contacting the optionally treated silica support with a monomeric zirconium or hafnium modifier metal compound to effect adsorption of the said modifier metal onto the support, typically to at least 25% of the said isolated silanol groups;
iii. optionally, removing any solvent or liquid carrier for the modifier metal compounds;
iv. optionally calcining the modified support for a time and temperature sufficient to convert the monomeric zirconium or hafnium compound adsorbed on the surface to an oxide or hydroxide of zirconium or hafnium in preparation for catalyst impregnation.

Preferably, the silanol group concentration is decreased prior to treatment with the modifier metal compounds by calcination treatment, chemical dehydration or other suitable methods.

Preferably, the modifier metal cation source herein is a solution of compounds of the said modifier metal so that the compounds are in solution when contacted with the support to effect adsorption onto the support.

Typically, the solvent for the said solution is other than water.

Typically, the solvent is an aliphatic alcohol, typically selected from C1-C6 alkanols such as methanol, ethanol, propanol, isopropanol, butanols, pentanols and hexanols, more typically, methanol, ethanol or propanols.

Advantageously, the proximity of the adsorbed modifier metal to neighbouring modifier metal cations may be controlled by the concentration of the said modifier metal in the contacting step and:—
a) the concentration of silanol groups on the silica support and/or
b) the size of any non-labile ligand attached to the modifier metal cation.

The silanol group concentration on the silica support prior to adsorption is preferably controlled by calcination or other suitable methods as known to those skilled in the art.

Methods of identification include for example L T Zhuravlev, in "Colloids and Surfaces: Physicochemical and Engineering Aspects, vol. 173, pp. 1-38, 2000" which describes four different forms of silanols: isolated silanols, geminal silanols, vicinal silanols, and internal silanols which can coexist on silica surfaces. Isolated silanol groups are most preferred. These can be identified by infrared spectroscopy as a narrow absorption peak at 3730-3750 cm$^{-1}$ whereas other silanols display broad peaks between 3460 and 3715 cm$^{-1}$ (see "The Surface Properties of Silicas, Edited by Andre P Legrand, john Wiley and Sons, 1998 (ISBN 0-471-95332-6) pp. 147-234).

By non-labile ligand is meant a ligand that is co-ordinated to the modifier metal and is not removed by the adsorption of the metal onto the silica surface. Accordingly, the non-labile ligand is typically coordinated to the modifier metal in solution prior to treatment of the silica surface with modifier metal. For the avoidance of doubt, the non-labile ligand is typically removed by treatment of the silica surface following adsorption of the modifier metal.

The size of the non-labile ligand is effective to space the modifier metals apart to prevent combination thereof.

According to further aspects of the present invention there is provided methods of producing catalyst or modified silica supports for a catalyst or catalysts according to the claims.

The invention extends to a modified silica support according to any of the aspects herein, wherein the support comprises isolated silanol groups (—SiOH) at a level of <2.5 groups per nm$^2$. Typically, the support comprises isolated silanol groups (—SiOH) at a level of >0.1 and <2.5 groups per nm$^2$, more preferably, at a level of from 0.2 to 2.2, most preferably, at a level of from 0.4 to 2.0 groups per nm$^2$.

Still further the invention extends to a catalyst or modified silica support according to any aspects herein, wherein the support comprises the said zirconium or hafnium modifier metal moieties having a total of up to 2 modifier metal atoms and/or derived from a monomeric and/or dimeric modifier metal cation source present on the support and present at a level of <2.5 moieties per nm$^2$.

Typically, the support comprises the said zirconium or hafnium modifier metal moieties at a level of >0.025 and <2.5 groups per nm$^2$, more preferably, at a level of from 0.05 to 1.5, most preferably, at a level of from 0.1 to 1.0 moieties per nm$^2$.

Suitable ligands herein may be non-labile ligands optionally selected from molecules with lone pair containing oxygen or nitrogen atoms able to form 5 or 6 membered rings with a zirconium or hafnium atom. Examples include diones, diimines, diamines, diols, dicarboxylic acids or derivatives thereof such as esters, or molecules having two different such functional groups and in either case with the respective N or O and N or O atom separated by 2 or 3 atoms to thereby form the 5 or 6 membered ring. Examples include pentane-2,4-dione, esters of 3-oxobutanoic acid with aliphatic alcohols containing 1-4 carbon atoms such as ethyl 3-oxobutanoate, propyl 3-oxobutanoate, isopropyl 3-oxobutanoate, n-butyl 3-oxobutanoate, t-butyl 3-oxobutanoate, heptane-3,5-dione, 2,2,6,6,-Tetramethyl-3,5-heptanedione, 1,2-ethanediol, 1,2-propanediol, 1,3-propanediol, 1,3-butanediol, 1,2-butanediol, 1,2-diaminoethane, ethanolamine, 1,2-diamino-1,1,2,2-tetracarboxylate, 2,3-dihydroxy-1,4-butanedioate, 2,4-dihydroxy-1,5-pentanedioate, salts of 1,2-dihydroxylbenzene-3-5-disulphonate, diethylenetriamine-pentaacetic acid, nitrolotriacetic acid, N-hydroxyethylethylenediaminetriacetic acid, N-hydroxyethyliminodiacetic acid, N,N-dihydroxyethylglycine, oxalic acid and its salts. Pentane-2,4-dione, heptane-3,5-dione, 2,2,6,6-Tetramethyl-3,5-heptanedione, ethyl 3-oxobutanoate and t-butyl 3-oxobutanoate are most preferred. The smaller bidentate ligands having, for example less than 10 carbon and/or hetero atoms in total enable small complexes to be formed which can allow higher concentrations to be deposited on the surface of the silica compared to larger ligands. Accordingly, the modifier metal cation source herein may be in the form of complexes of zirconium and/or hafnium with such smaller ligands, preferably, with at least one such ligand. Such compounds may include labile ligands such as solvent ligands, for example in alcohol solvent, alkoxide ligands such as ethoxide or propoxide etc, or perchlorate, oxynitrate and oxychloride ligands.

The concentration of preferably isolated silanol groups determines the maximum number of sites for modifier metal adsorption. By controlling this concentration, the proximity of the adsorbed modifier metal can be effectively determined because the distribution of silanol sites will generally be homogeneous. The silanol concentration for the production of a modified silica support according to the present inventions may be below 2.5 groups per nm$^2$, more typically, less than 1.5 groups per nm$^2$, most typically, less than 0.8 groups per nm$^2$. Suitable ranges for the silanol concentration for production of a modified silica supports may be 0.1-2.5 silanol groups per nm$^2$, more preferably 0.15-1.0 silanol groups per nm$^2$, most preferably 0.2-0.7 silanol groups per nm$^2$.

The concentration of the modifier metal, generally in the form of a cation should be set at a level that prevents the significant formation of bilayers etc. on the surface of the support which would lead to modifier metal to metal interaction. In addition, filling in of gaps in the initial monolayer that could result in weak adsorption of the modifier metal away from silanol sites should also be avoided to prevent interaction with neighbouring strongly adsorbed modifier metals. Typical concentration ranges for the modifier metals of the invention may be as set out herein.

Typically, at least 30%, such as at least 35%, more preferably at least 40%, such as at least 45%, most suitably at least 50%, such as at least 55%, for example at least 60% or 65%, and most preferably at least 70% such as at least 75% or 80%, more typically, at least 85%, most typically, at least 90%, especially, at least 95% of the modifier metal in the modifier metal compounds are dimeric and/or monomeric modifier metal compounds when the source thereof is contacted with the support to effect adsorption of the said compounds onto the support, more typically, monomeric.

According to a further aspect of the present invention there is provided a method of producing a catalyst comprising
a modified silica support,
the modified silica support comprising a modifier metal;
and a catalytic metal on the modified silica support,
wherein the modifier metal is selected from one or more of zirconium and/or hafnium,
characterised in that at least a proportion, typically, at least 25%, of the said modifier metal is present in the form of monomeric modifier metal moieties
the said method comprising
the steps of:—
treating the silica support to provide isolated silanol groups (—SiOH) at a level <2.5 groups per nm$^2$;
reacting the treated support with monomeric zirconium or hafnium monomeric modifier metal compounds to effect bonding thereof to at least 25% of the said isolated silanol groups;
optionally, removing any solvent or liquid carrier;
calcining the modified silica for a time and temperature sufficient to convert the monomeric zirconium or hafnium compound adsorbed on the surface to an oxide or hydroxide of zirconium or hafnium;
treating the said calcined modified silica with a catalytic alkali metal to impregnate the modified silica with the catalytic metal.

Advantageously, by providing a smaller number of isolated silanol sites and by bonding monomeric zirconium or hafnium species to these sites a catalyst support is provided that leads to improved selectivity of the catalyst, lower sintering rate and better ageing of catalyst.

A suitable method of treating the silica to provide the isolated silanol groups at the level specified is by calcination. However, other techniques such as hydrothermal treatment or chemical dehydration are also possible. U.S. Pat. No. 5,583,085 teaches chemical dehydration of silica with dimethyl carbonate or ethylene dicarbonate in the presence of an amine base. U.S. Pat. Nos. 4,357,451 and 4,308,172 teach chemical dehydration by chlorination with $SOCl_2$ followed by dechlorination with $H_2$ or ROH followed by oxygen in a dry atmosphere. Chemical dehydration may provide up to 100% removal of silanols against a minimum of 0.7/nm$^2$ by thermal treatment. Thus, in some instances, chemical dehydration may provide more scope for silanol group control.

The term isolated silanol (also known as single silanol) is well known in the art and distinguishes the groups from vicinal or geminal or internal silanols. Suitable methods for determining the incidence of isolated silanols include surface sensitive infrared spectroscopy and $^1$H NMR or $^{31}$Si NMR.

According to a fifth aspect of the present invention there is provided a method of producing a catalyst according to any previous aspects of the present invention, comprising the steps of: forming a modified silica according to any previous aspect, and contacting the modified silica support with a solution containing a catalytic metal to impregnate the modified silica with the catalytic metal.

Preferably, the silica support is dried or calcined prior to treatment with the modifier metal cation source. The modified silica formed may irrespective of whether previously dried or calcined be dried or calcined prior to addition of the catalytic metal.

The silica may be in the form of a gel prior to treatment with the modifier metal. The gel may be in the form of a hydrogel, a xerogel or an aerogel at the commencement of modification.

The silica support may be a xerogel, hydrogel or aerogel. Preferably, the silica support is a xerogel.

The silica support may be treated by the metal cation source by any of the various techniques known to those skilled in the art of support formation. The silica support may be contacted with the metal cation source in such a manner so as to disperse modifier metal throughout the silica support. Typically, the zirconium and/or hafnium may be homogeneously dispersed throughout the silica support. Preferably, modifier metal is dispersed through the silica support by adsorption.

By the term "adsorption" or the like in relation to the modifier metal as used herein is meant the incorporation of modifier metal onto the silica support surface by the interaction of the metal cation source with the silica support, typically by chemisorption. Typically, addition of the modifier to the silica support involves the steps of: adsorption of the metal cation source onto the silica support to form an organic metal complex and calcination of the complex to convert the organic metal complexes to metal oxide moieties. Typically, there is therefore a homogeneous dispersion of modifier metal throughout the silica support. Typically, zirconium and/or hafnium is dispersed throughout the silica support.

Examples of suitable metal cation sources herein include organic complexes such as zirconium (pentane-2,4-dione)$_4$, zirconium(ethyl 3-oxobutanoate)$_4$, zirconium(heptane-3,5-dione)$_4$, zirconium(2,2,6,6-tetramethylheptane-3,5-dione)$_4$, zirconium(propoxide) (pentance-2-3-dione)$_3$, zirconium (propoxide)$_3$ (2,2,6,6-tetramethyl-3,5-heptanedione), (zirconium(Ot-butyl)$_3$(t-butyl 3-oxobutanoate), zirconium(Ot-butyl)$_2$(t-butyl 3-oxobutanoate)$_2$.

Typically, the metal cation source is provided as an organic complex. Typically, the modifier metal is contacted with the silica support in solution.

Preferably, the metal cation source is provided in any solvent in which the metal cation source is soluble. Examples of suitable solvent include water or alcohols. Preferred solvents are alcohols such as methanol, ethanol, propanol, isopropanol, butanols, pentanols and hexanols.

Preferably, the metal cation source is added to the silica as a metal salt in such alcoholic solution.

In one embodiment, the metal cation source is provided as a solution of one or more of zirconium(IV)acetylacetonate (zirconium,tetrakis(2,4-pentanedionato-O,O')), zirconium (heptane-3,5-dione)$_4$, zirconium(2,2,6,6-tetramethyl-3,5-heptanedione)$_4$, zirconium(IV) ethyl 3-oxobutanoate, zirconium(IV) t-butyl 3-oxobutanoate, or zirconium(IV) i-propyl 3-oxobutanoate in one of methanol, ethanol, isopropanol, propanol, butanol, isobutanol, or 2-butanol.

Preferably, after adsorption of the modifier metal onto the silica support, the solvent is removed by evaporation.

Optionally, the modified silica support is calcined to remove any ligands or other organics from the modified support.

It will be understood by a skilled person that the catalytic metal may be added to the modified silica by any suitable means. Typically, in order to produce the modified silica catalyst, the modified silica is contacted with a catalytic metal.

Typically, in order to produce the catalyst, the modified silica support is contacted with an acidic, neutral or alkaline aqueous solution containing a catalytic metal such as caesium, in the form of a salt of a catalytic metal and a base. Alternatively, the support can be contacted with a water miscible solution of the catalytic metal salt in an organic solvent. Preferred solvents are alcohols such as methanol, ethanol, propanol and isopropanol, preferably methanol. The most preferred solvent is methanol. Most preferably, the catalytic metal is added as a salt solution in methanol. Low levels of water, typically up to 20 vol % can be contained in the solutions.

Typically, the conditions of temperature, contact time and pH during this stage of the catalyst production process are such as to allow for impregnation of the modified silica support with the catalytic metal to form a modified silica supported catalyst.

Typical conditions of temperature for this step are between 5-95° C., more typically 10-80° C. and most typically between 20-70° C. The temperature for this step may be at least 5° C., more typically at least 10° C., most typically, at least 20° C.

Typical contact times between the modified support and the catalytic metal containing solution for this step may be between 0.05-48 hours, more typically between 0.1-24 hours, most typically between 0.5-18 hours. The contact time may be at least 0.05 hours, more typically at least 0.1 hours, most typically at least 0.5 hours.

The concentration of the catalytic metal salt solution for this step is dependent on a large number of factors including the solubility limit of the catalytic metal compound, the porosity of the modified silica support, the desired loading of the catalytic metal on the support and the method of addition, including the amount of liquid used to impregnate the support, the pH and the choice of the catalytic metal compound. The concentration in solution is best determined by experiment.

Suitable salts of catalytic metals for incorporation of the catalytic metal generally may be selected from one or more of the group consisting of formate, acetate, propionate, hydrogen carbonate, chloride, nitrate, hydroxide and carbonate, more typically, hydroxide, acetate or carbonate and most typically hydroxide and/or carbonate. The pH can be controlled during the impregnation by addition of ammonia with the metal compound or by using an appropriate catalytic metal compound such as the formate, carbonate, acetate or hydroxide, more preferably, the hydroxide or carbonate, in all cases either alone, in combination, or together with an appropriate carboxylic acid. The control of the pH in the preferred ranges is most important at the end of the impregnation to effect satisfactory adsorption. Most typically, these salts may be incorporated using an alkaline solution of the salt. If the salt is not itself alkaline then a suitable base such as ammonium hydroxide may be added. As hydroxide salts are basic in nature, mixtures of one or more of the above salts with the hydroxide salt of the particular catalytic metal such as caesium may conveniently be prepared.

It will be understood by the skilled person that a catalytic metal of the present invention may be added to the modified silica support by any suitable means. The catalyst may be fixed, typically by calcination, onto the support after deposition of the compound onto the support optionally using a suitable aqueous salt and subsequent drying of the surface coated support.

Generally, drying of the modified silica support is achieved by appropriate methods known to the skilled person such as in a drying unit or oven.

Typically, the catalyst contains between 0.01-25% w/w water, more typically 0.1-15% w/w water and most typically between 0.5%-5.0 w/w water.

Optionally, the modified silica supported catalyst containing catalytic metal may be dried or calcined, the process of calcination is well known to those skilled in the art.

In some cases, it may be necessary to calcine the support formed from the modification stage at 200-1000° C., more typically, 300-800° C., most typically, 350-600° C. prior to addition of the catalytic metal. In preferred calcinations of the support formed from the modification stage, the temperature is at least 375° C., such as 400° C. or 450° C. The calcination atmosphere should typically contain some oxygen, suitably 1-30% oxygen and most suitably 2-20% oxygen to effect removal of the organic residues as carbon dioxide and water. The calcination time may typically be between 0.01 and 100 hours, suitably 0.5-40 hours, most suitably 1-24 hours. The calcined support such as xerogel material should be cooled to the appropriate temperature for impregnation. Addition of the catalytically active metal can be carried out by methods described for the uncalcined material or can be by any other normal method used to impregnate catalyst supports, such as xerogel supports, such as using a solvent other than water such as an alcohol, suitably methanol, ethanol, propanol or isopropanol or using the incipient wetness method where only sufficient solution is added to the xerogel supports to fill the pores of the xerogel support. In this case, the concentration of the catalytically active metal may be calculated so as to introduce the target amount of catalytically active metal to the xerogel support material rather than providing an excess of solution of lower concentration by the method described earlier. The addition of the catalytically active metal may utilise any preferred methodology known in the art. The calcining technique is particularly advantageous where an organic complex is used as the source of the zirconium and/or hafnium as it may be necessary to modify the subsequent catalyst preparation procedure so as to remove at least a fraction of the organic complexing salt prior to impregnation with caesium. Advantageously, it has been found that the catalytic metal:modifier metal ratio and therefore the catalytic metal required is lowered by the calcination of the modified support. This was unexpected and provides a further improvement to the invention.

According to a sixth aspect of the present invention there is provided a method of producing an ethylenically unsaturated carboxylic acid or ester, typically, an α, β ethylenically unsaturated carboxylic acid or ester, comprising the steps of contacting formaldehyde or a suitable source thereof with a carboxylic acid or ester in the presence of catalyst and optionally in the presence of an alcohol, wherein the catalyst is according to the first or any of the other aspects of the present invention defined herein.

Advantageously, it has also been found that catalysts comprising modified silicas as defined herein and containing a catalytic metal are remarkably effective catalysts for the production of α, β ethylenically unsaturated carboxylic acid or esters by condensation of the corresponding acid or ester with a methylene source such as formaldehyde having reduced sintering of the catalyst surface, improved selectivity and providing high catalyst surface area. In particular enhanced properties are found when using monomeric and/or dimeric modifier metal moieties and/or when the modified silica support is calcined prior to treatment with the catalytic metal. Furthermore, the use of certain metal complexes to incorporate the modifier metal onto the support by adsorption provides a convenient source of monomeric and/or dimeric modifier metal moieties. Such a source also allows control of the nature of the modifier metal and provides a more uniform distribution of modifier metal moieties.

By the term "a suitable source thereof" in relation to formaldehyde of the fourth aspect of the present invention is meant that the free formaldehyde may either form in situ from the source under reaction conditions or that the source may act as the equivalent of free formaldehyde under reaction conditions, for example it may form the same reactive intermediate as formaldehyde so that the equivalent reaction takes place.

A suitable source of formaldehyde may be a compound of formula (I):

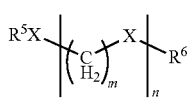

(I)

wherein $R^5$ and $R^6$ are independently selected from $C_1$-$C_{12}$ hydrocarbons or H, X is O, n is an integer from 1 to 100, and m is 1.

Typically, $R^5$ and $R^6$ are independently selected from $C_1$-$C_{12}$ alkyl, alkenyl or aryl as defined herein, or H, more suitably, $C_1$-$C_{10}$ alkyl, or H, most suitably, $C_1$-$C_6$ alkyl or H, especially, methyl or H. Typically, n is an integer from 1 to 10, more suitably 1 to 5, especially, 1-3.

However, other sources of formaldehyde may be used including trioxane.

Therefore, a suitable source of formaldehyde also includes any equilibrium composition which may provide a source of formaldehyde. Examples of such include but are not restricted to dimethoxymethane, trioxane, polyoxymethylenes $R^1$—O—$(CH_2$—O)—$R^2$ wherein $R^1$ and/or $R^2$ are alkyl groups or hydrogen, i=1 to 100, paraformaldehyde, formalin (formaldehyde, methanol, water) and other equilibrium compositions such as a mixture of formaldehyde, methanol and methyl propionate.

Polyoxymethylenes are higher formals or hemiformals of formaldehyde and methanol $CH_3$—O—$(CH_2$—O)$_i$—$CH_3$ ("formal-i") or $CH_3$—O—$(CH_2$—O)$_i$—H ("hemiformal-i"), wherein i=1 to 100, suitably, 1-5, especially 1-3, or other polyoxymethylenes with at least one non methyl terminal group. Therefore, the source of formaldehyde may also be a polyoxymethylene of formula $R^{31}$—O—$(CH2$-O—$)_i R^{32}$, where $R^{31}$ and $R^{32}$ may be the same or different groups and at least one is selected from a $C_1$-$C_{10}$ alkyl group, for instance $R^{31}$=isobutyl and $R^{32}$=methyl.

Generally, the suitable source of formaldehyde is selected from dimethoxymethane, lower hemiformals of formaldehyde and methanol, $CH_3$—O—$(CH_2$—O)$_i$—H where i=1-3, formalin or a mixture comprising formaldehyde, methanol and methyl propionate.

Typically, by the term formalin is meant a mixture of formaldehyde:methanol:water in the ratio 25 to 65%: 0.01 to 25%: 25 to 70% by weight. More typically, by the term formalin is meant a mixture of formaldehyde:methanol:water in the ratio 30 to 60%: 0.03 to 20%: 35 to 60% by weight. Most typically, by the term formalin is meant a mixture of formaldehyde:methanol:water in the ratio 35 to 55%: 0.05 to 18%: 42 to 53% by weight.

Typically, the mixture comprising formaldehyde, methanol and methyl propionate contains less than 5% water by weight. More suitably, the mixture comprising formaldehyde, methanol and methyl propionate contains less than 1% water by weight. Most suitably, the mixture comprising formaldehyde, methanol and methyl propionate contains 0.1 to 0.5% water by weight.

According to a seventh aspect of the present invention, there is provided a process for preparing an ethylenically unsaturated acid or ester comprising contacting an alkanoic acid or ester of the formula $R^1$—$CH_2$—$COOR^3$, with formaldehyde or a suitable source of formaldehyde of formula (I) as defined below:

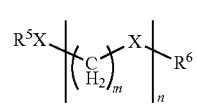

(I)

where R5 is methyl and R6 is H;
X is O;
m is 1;
and n is any value between 1 and 20 or any mixture of these;
in the presence of a catalyst according to any aspect of the present invention, and optionally in the presence of an alkanol; wherein R1 is hydrogen or an alkyl group with 1 to 12, more Suitably, 1 to 8, most suitably, 1 to 4 carbon atoms and R3 may also be independently, hydrogen or an alkyl group with 1 to 12, more suitably, 1 to 8, most suitably, 1 to 4 carbon atoms.

Therefore, the present inventors have discovered that having zirconium and/or hafnium in the form of metal oxide moieties according to the present invention enables surprising improvement in selectivity for the condensation of methylene sources such as formaldehyde with a carboxylic acid or alkyl ester such as methyl propionate to form ethylenically unsaturated carboxylic acids. In addition, the rate of sintering of the catalyst surface during the condensation reaction is significantly and surprisingly reduced.

Accordingly, one particular process for which the catalysts of the present invention have been found to be particularly advantageous is the condensation of formaldehyde with methyl propionate in the presence of methanol to produce MMA.

In the case of production of MMA, the catalyst is typically contacted with a mixture comprising formaldehyde, methanol and methyl propionate.

The process of the sixth or seventh aspect of the invention is particularly suitable for the production of acrylic and alkacrylic acids and their alkyl esters, and also methylene substituted lactones. Suitable methylene substituted lactones include 2-methylene valerolactone and 2-methylene butyrolactone from valerolactone and butyrolactone respectively. Suitable, (alk)acrylic acids and their esters are ($C_{0-8}$alk) acrylic acid or alkyl ($C_{0-8}$alk)acrylates, typically from the reaction of the corresponding alkanoic acid or ester thereof with a methylene source such as formaldehyde in the presence of the catalyst, suitably the production of methacrylic acid, acrylic acid, methyl methacrylate, ethyl acrylate or butyl acrylate, more suitably, methacrylic acid or especially methyl methacrylate(MMA) from propanoic acid or methyl propionate respectively. Accordingly, in the production of methyl methacrylate or methacrylic acid, the preferred ester or acid of formula $R^1$—$CH_2$—$COOR^3$ is methyl propionate or propionic acid respectively and the preferred alkanol is therefore methanol. However, it will be appreciated that in the production of other ethylenically unsaturated acids or esters, the preferred alkanols or acids will be different.

The reaction of the present invention may be a batch or continuous reaction.

Typical conditions of temperature and gauge pressure in the process of the sixth or seventh aspect of the invention are between 100° C. and 400° C., more preferably, 200° C. and 375° C., most preferably, 275° C. and 360° C.; and/or between 0.001 MPa and 1 MPa, more preferably between 0.03 MPa and 0.5 MPa, most preferably between 0.03 MPa and 0.3 MPa. Typical residence times for the reactants in the presence of the catalyst are between 0.1 and 300 secs, more preferably between, 1-100 secs, most preferably between 2-50 secs, especially, 3-30 secs.

The amount of catalyst used in the process of production of product in the present invention is not necessarily critical and will be determined by the practicalities of the process in which it is employed. However, the amount of catalyst will generally be chosen to effect the optimum selectivity and yield of product and an acceptable temperature of operation. Nevertheless, the skilled person will appreciate that the minimum amount of catalyst should be sufficient to bring about effective catalyst surface contact of the reactants. In addition, the skilled person would appreciate that there would not really be an upper limit to the amount of catalyst relative to the reactants but that in practice this may be governed again by the contact time required and/or economic considerations.

The relative amount of reagents in the process of the sixth or seventh aspect of the invention can vary within wide limits but generally the mole ratio of formaldehyde or suitable source thereof to the carboxylic acid or ester is within the range of 20:1 to 1:20, more suitably, 5:1 to 1:15. The most preferred ratio will depend on the form of the formaldehyde and the ability of the catalyst to liberate formaldehyde from the formaldehydic species. Thus highly reactive formaldehydic substances where one or both of $R^{31}$ and $R^{32}$ in $R^{31}$O—($CH_2$—O)$R^{32}$ is H require relatively low ratios, typically, in this case, the mole ratio of formaldehyde or suitable source thereof to the carboxylic acid or ester is within the range of 1:1 to 1:9. Where neither of $R^{31}$ and $R^{32}$ is H, as for instance in $CH_3$O—$CH_2$—$OCH_3$, or in trioxane higher ratios are most preferred, typically, 6:1 to 1:3.

As mentioned above, due to the source of formaldehyde, water may also be present in the reaction mixture. Depending on the source of formaldehyde, it may be necessary to remove some or all of the water therefrom prior to catalysis. Maintaining lower levels of water than that in the source of formaldehyde may be advantageous to the catalytic efficiency and/or subsequent purification of the products. Water at less than 10 mole % in the reactor is preferred, more suitably, less than 5 mole %, most suitably, less than 2 mole %.

The molar ratio of alcohol to the acid or ester is typically within the range 20:1 to 1:20, preferably 10:1 to 1:10, most preferably 5:1 to 1:5, for example 1:1.5. However, the most preferred ratio will depend on the amount of water fed to the catalyst in the reactants plus the amount produced by the reaction, so that the preferred molar ratio of the alcohol to the total water in the reaction will be at least 1:1 and more preferably at least 2:1.

The reagents of the sixth or seventh aspect may be fed to the reactor independently or after prior mixing and the process of reaction may be continuous or batch. Typically, however, a continuous process is used.

Typically, the method of the sixth or seventh aspect of the present invention is carried out when reactants are in the gaseous phase.

In a still further aspect, the invention extends to the process of producing an ethylenically unsaturated carboxylic acid or ester according to any of the relevant aspects herein comprising the steps of first producing a catalyst according to any of the relevant aspects herein.

Definitions

The term "alkyl" when used herein, means, unless otherwise specified, $C_1$ to $C_{12}$ alkyl and includes methyl, ethyl, ethenyl, propyl, propenyl butyl, butenyl, pentyl, pentenyl, hexyl, hexenyl and heptyl groups, typically, the alkyl groups are selected from methyl, ethyl, propyl, butyl, pentyl and hexyl, more typically, methyl. Unless otherwise specified, alkyl groups may, when there is a sufficient number of carbon atoms, be linear or branched, be cyclic, acyclic or part cyclic/acyclic, be unsubstituted, substituted or terminated by one or more substituents selected from halo, cyano, nitro, —$OR^{19}$, —$OC(O)R^{20}$, —$C(O)R^{21}$, —$C(O)OR^{22}$, —$NR^{23}R^{24}$, —$C(O)NR^{25}R^{26}$, —$SR^{29}$, —$C(O)SR^{30}$, —$C(S)NR^{27}R^{28}$, unsubstituted or substituted aryl, or unsubstituted or substituted Het, wherein $R^{19}$ to $R^{30}$ here and generally herein each independently represent hydrogen, halo, unsubstituted or substituted aryl or unsubstituted or substituted alkyl, or, in the case of $R^{21}$, halo, nitro, cyano and amino and/or be interrupted by one or more (typically less than 4) oxygen, sulphur, silicon atoms, or by silano or dialkylsilcon groups, or mixtures thereof. Typically, the alkyl groups are unsubstituted, typically, linear and typically, saturated.

The term "alkenyl" should be understood as "alkyl" above except at least one carbon-carbon bond therein is unsaturated and accordingly the term relates to $C_2$ to $C_{12}$ alkenyl groups.

The term "alk" or the like should, in the absence of information to the contrary, be taken to be in accordance with the above definition of "alkyl" except "$C_0$ alk" means non-substituted with an alkyl.

The term "aryl" when used herein includes five-to-ten-membered, typically five to eight membered, carbocyclic aromatic or pseudo aromatic groups, such as phenyl, cyclopentadienyl and indenyl anions and naphthyl, which groups may be unsubstituted or substituted with one or more substituents selected from unsubstituted or substituted aryl, alkyl (which group may itself be unsubstituted or substituted or terminated as defined herein), Het (which group may itself be unsubstituted or substituted or terminated as defined herein), halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $SR^{29}$, $C(O)SR^{30}$ or $C(S)NR^{27}R^{28}$ wherein $R^{19}$ to $R^{30}$ each independently represent hydrogen, unsubstituted or substituted aryl or alkyl (which alkyl group may itself be unsubstituted or substituted or terminated as defined herein), or, in the case of $R^{21}$, halo, nitro, cyano or amino.

The term "halo" when used herein means a chloro, bromo, iodo or fluoro group, typically, chloro or fluoro.

The term "Het", when used herein, includes four- to twelve-membered, typically four- to ten-membered ring systems, which rings contain one or more heteroatoms selected from nitrogen, oxygen, sulfur and mixtures thereof, and which rings contain no, one or more double bonds or may be non-aromatic, partly aromatic or wholly aromatic in character. The ring systems may be monocyclic, bicyclic or fused. Each "Het" group identified herein may be unsubstituted or substituted by one or more substituents selected from halo, cyano, nitro, oxo, alkyl (which alkyl group may itself be unsubstituted or substituted or terminated as defined herein) —$OR^{19}$, —$OC(O)R^{20}$, —$C(O)R^{21}$, —$C(O)OR^{22}$, —$N(R^{23})R^{24}$, —$C(O)N(R^{25})R^{26}$, —$SR^{29}$, —$C(O)SR^{30}$ or —$C(S)N(R^{27})R^{28}$ wherein $R^{19}$ to $R^{30}$ each independently represent hydrogen, unsubstituted or substituted aryl or alkyl (which alkyl group itself may be unsubstituted or substituted or terminated as defined herein) or, in the case of $R^{21}$, halo, nitro, amino or cyano. The term "Het" thus includes groups such as optionally substituted azetidinyl, pyrrolidinyl, imidazolyl, indolyl, furanyl, oxazolyl, isoxazolyl, oxadiazolyl, thiazolyl, thiadiazolyl, triazolyl, oxatriazolyl, thiatriazolyl, pyridazinyl, morpholinyl, pyrimidinyl, pyrazinyl, quinolinyl, isoquinolinyl, piperidinyl, pyrazolyl and piperazinyl. Substitution at Het may be at a carbon atom of the Het ring or, where appropriate, at one or more of the heteroatoms.

"Het" groups may also be in the form of an N oxide.

Suitable optional alcohols for use in the catalysed reaction of the fourth and fifth aspects of the present invention may be selected from: a $C_1$-$C_{30}$ alkanol, including aryl alcohols, which may be optionally substituted with one or more substituents selected from alkyl, aryl, Het, halo, cyano, nitro, $OR^{19}$, $OC(O)R^{20}$, $C(O)R^{21}$, $C(O)OR^{22}$, $NR^{23}R^{24}$, $C(O)NR^{25}R^{26}$, $C(S)NR^{27}R^{28}$, $SR^{29}$ or $C(O)SR^{30}$ as defined herein. Highly preferred alkanols are $C_1$-$C_8$ alkanols such as methanol, ethanol, propanol, iso-propanol, isobutanol, t-butyl alcohol, phenol, n-butanol and chlorocapryl alcohol, especially, methanol. Although the monoalkanols are most preferred, poly-alkanols, typically, selected from di-octa ols such as diols, triols, tetra-ols and sugars may also be utilised. Typically, such polyalkanols are selected from 1, 2-ethanediol, 1,3-propanediol, glycerol, 1,2,4 butanetriol, 2-(hydroxymethyl)-1,3-propanediol, 1,2,6 trihydroxyhexane, pentaerythritol, 1,1,1 tri(hydroxymethyl)ethane, nannose, sorbase, galactose and other sugars. Preferred sugars include sucrose, fructose and glucose. Especially preferred alkanols are methanol and ethanol. The most preferred alkanol is methanol. The amount of alcohol is not critical. Generally, amounts are used in excess of the amount of substrate to be esterified. Thus the alcohol may serve as the reaction solvent as well, although, if desired, separate or further solvents may also be used.

The term ageing is described in, for example, patent application WO 2009/003722. The general principles of ageing are described in The Chemistry of Silica: Solubility, Polymerisation, Colloid and Surface Properties and Biochemistry of Silica: by Ralph K Iler, 1979, John Wiley and Sons Inc., ISBN 0-471-02404-X, pages 358-364. If this stage is undertaken, the hydrogel is then washed again to remove any materials used in the ageing process and to bring the solution to the correct pH for addition of catalytically active metal which depends on the choice of salt for the catalytically active metal.

Although the metal, metal oxide and metal oxide moieties of any aspect of the present invention or any preferred or optional feature thereof may be zirconium or hafnium and zirconia or hafnia respectively, they are typically, zirconium and zirconia and moieties of zirconia.

The term "gel" as used herein is also known to the skilled person but in case of doubt may be taken to be a solid network in which a fluid is dispersed. Generally, the gel is a polymer network in which fluid is dispersed. A co-gel is a term used to indicate that more than one original chemical compound/moiety is incorporated into the polymeric network, usually silica and a metal oxide or salt such as zirconia. Accordingly, co-gelation herein means the formation of a co-gel.

A gel is thus a sol that has set. A Hydrogel is thus a gel as defined herein where the fluid is water. A Xerogel is a gel that has been dried to remove the fluid. An Aerogel is a gel in which the fluid is replaced by a gas and therefore is not subject to the same shrinkage as a Xerogel.

The term commencement herein means the beginning of the formation of the modified silica.

The term "moieties" as used herein in relation to the metal is used to refer to the form of the modifier metal on the modified support. Although, the modifier metal generally forms part of a network, the modifier metal will be in the form of discrete residues on the silica substrate. Reference to a total of up to two metal atoms or the like should be taken to refer to the monomeric and/or the dimeric form of the residue thereof. Suitably in the aspects of the present invention herein, it has been found to be advantageous to have the moieties in the form of a monomeric residue. Accordingly, the term up to 2 modifier metal atoms or the like herein means a total of 1 and/or 2 modifier metal atoms. Herein, 1 is preferred to 2 modifier metal atoms, especially preferred is a total of 1 and/or 2 zirconium atoms in the said moieties, most especially 1 zirconium atom in the moieties.

The term monomeric or dimeric means having monomer like or dimer like form or in the case of residues on the silica i.e. having the form of a monomer or dimer residue.

% of the modifier metal has no units herein because it refers to number of metal atoms per total number of such atoms. It will be appreciated that the moieties may take the form of non-monomeric or non-dimeric clusters but that these clusters are still made up of modifier metal atoms.

Embodiments of the invention will now be defined by reference to the accompanying examples and figures in which:

FIG. 1 shows the HRTEM image for the Zr modified silica example 5;

FIG. 2 shows the HRTEM image for the Zr modified silica example 7;

FIG. 3 shows the HRTEM image for the Zr modified silica example 14;

FIG. 4 shows the HRTEM image for the Zr modified silica example 15;

FIG. 5 shows the HRTEM image for the Zr modified silica example 17; and

FIG. 6 shows the HRTEM image for the Zr modified silica example 18;

FIG. 7 shows the MMA+MAA selectivity (%) vs. catalyst activity for the catalysts prepared in Example 20 to Example 74;

FIG. 8 shows the catalyst selectivity for mixed monomer/trimer catalysts prepared in Example 75 to Example 79; and FIG. 9 shows the catalyst sintering constants as determined by the advanced ageing test described in Example 81.

EXPERIMENTAL

Silica Support Description

Example 1

Fuji Silysia CARiACT Q10 silica (Q10) was dried in a laboratory oven at 160° C. for 16 hours, after which it was removed from the oven and cooled to room temperature in a sealed flask stored in a desiccator. This silica had a surface area of 333 m$^2$/g, a pore volume of 1.0 ml/g, and an average pore diameter of 10 nm as determined by nitrogen adsorption/desorption isotherm analysis (Micromeretics Tristar II). A silanol number of 0.8 OH/nm$^2$ was found through TGA analysis. This silica is primarily composed of spherical silica beads in the diameter range of 2-4 mm.

Example 2

Fuji Silysia CARiACT Q30 silica (Q30) was calcined in a tubular furnace at 900° C. for 5 hours with a heating ramp rate of 5° C./min under a flow of nitrogen gas. It was then cooled down to room temperature and stored in a sealed flask in a desiccator. This silica had a surface area of 112 m$^2$/g, a pore volume of 1.0 ml/g, an average pore diameter of 30 nm and is primarily composed of spherical silica beads in the diameter range of 2-4 mm.

Zr Modification of Silica Supports

Example 3 (0.92 wt % Zr, Monomeric Zr on Q10)

0.542 g of, Zr(acac)$_4$ (97%, Sigma Aldrich) was dissolved in 11 ml of MeOH (99% Sigma Aldrich). In a separate flask 10 g of the silica from Example 1 was weighed off. The weighed off silica was then added to the Zr(acac)$_4$ solution with agitation. Agitation was continued until all of the Zr(acac)$_4$ solution had been taken up into the pore volume of the silica. Once pore filling had been completed the Zr-modified silica was left for 16 hours in a sealed flask with periodic agitation. After this time the extra-porous solution was removed by filtration. This was followed by a drying step where the intra-porous organic solvent was removed by passing a flow of nitrogen gas over the wet Zr-modified silica at room temperature. Alternatively, the intra-porous solvent was removed on a rotary evaporator at reduced pressure. Once all of the solvent had been removed the Zr-modified silica support was calcined in a tubular furnace at 500° C. under a flow of air (1 l/min) with a heating ramp rate of 5° C./min and a final hold of 5 hours. Upon cooling this yielded the Zr grafted silica support with a 100% Zr usage efficiency. The Zr load (wt %) on the Zr-modified support was determined via powder Energy Dispersive X-Ray Fluorescence analysis (Oxford Instruments X-Supreme8000).

Example 4 (1.5 wt % Zr, Monomeric Zr on Q10)

A support modification as described in Example 3 was performed except that 0.874 g of Zr(acac)$_4$ was used.

Example 5 (2.3 wt % Zr, Monomeric Zr on Q10)

A support modification as described in Example 3 was performed except that 1.38 g of Zr(acac)$_4$ was used and 20 ml of 1-PrOH (99% Sigma Aldrich) was used instead of MeOH. Additionally, agitation was continued throughout the 16 h ageing step prior to solvent removal. This resulted in a 90% Zr usage efficiency.

Example 6 (2.7 wt % Zr, Monomeric Zr on Q10)

A support modification as described in Example 5 was performed except that 1.67 g of Zr(acac)$_4$ was used and 20 ml of MeOH (99% Sigma Aldrich) was used instead of 1-PrOH. This resulted in an 89% Zr usage efficiency.

Example 7 (4.2 wt % Zr, Monomeric Zr on Q10)

A support modification as described in Example 5 was performed except that 2.56 g of Zr(acac)$_4$ was used and 20 ml of toluene (99% Sigma Aldrich) was used instead of 1-PrOH. This resulted in a 93% Zr usage efficiency.

Example 8 (0.7 wt % Zr, Monomeric Zr on Q30)

A support modification as described in Example 6 was performed except that 0.43 g of Zr(acac)$_4$ was used and silica from Example 2 was used. This resulted in a 93% Zr usage efficiency.

Example 9 (1.1 wt % Zr, Monomeric Zr on Q10)

A support modification as described in Example 5 was performed except that 2.15 g of Zr(thd)$_4$ was used and 20 ml of MeOH was used instead of 1-PrOH. This resulted in a 47% Zr usage efficiency.

Example 10 (2.2 wt % Zr, Monomeric Zr on Q10)

A support modification as described in Example 9 was performed except 20 ml of toluene was used instead of MeOH. This resulted in a 93% Zr usage efficiency.

Example 11 (3.9 wt % Zr, Monomeric Zr on Q10)

A support modification as described in Example 5 was performed except that 3.19 g of Zr(EtOAc)$_4$ was used and 20 ml of heptane (99% Sigma Aldrich) was used instead of 1-PrOH. This resulted in an 86% Zr usage efficiency.

Example 12 (6.7 wt % Zr, Dimeric Zr on Q10)

A support modification as described in Example 5 was performed except that 3.12 g of [Zr(OPr)$_3$(acac)]2 was used and 20 ml of heptane was used instead of 1-PrOH. This resulted in a 95% Zr usage efficiency.

Example 13 (2.2 wt % Zr, Trimeric Zr on Q30) (Comparative)

A support modification as described in Example 5 was performed except that 1.16 g of Zr(nOPr)$_4$ (70 wt % in 1-propanol, Sigma Aldrich). Additionally 10 g of silica from Example 2 was used instead of the silica from Example 1. This resulted in a 100% Zr usage efficiency.

Example 14 (6.0 wt % Zr, Trimeric Zr on Q10) (Comparative)

A support modification as described in Example 5 was performed except that 3.35 g of Zr(nOPr)$_4$ (70 wt % in 1-propanol, Sigma Aldrich). This resulted in a 100% Zr usage efficiency.

Example 15 (8.0 wt % Zr, Pentameric Zr on Q10) (Comparative)

A support modification as described in Example 5 was performed except that 2.67 g of zirconium(IV) ethoxide (97% Sigma Aldrich) was dissolved 20 ml of ethanol (anhydrous, Sigma Aldrich) with 1.77 g of acetic acid (glacial, Sigma Aldrich) instead of 1-PrOH. This resulted in a 100% Zr usage efficiency.

Hf Modification of Silica Supports

Example 16 (5.4 wt % Hf, Monomeric Hf on Q10)

A support modification as described in Example 5 was performed except that 1.37 g of Hf(iOPr)$_4$ (99% Sigma Aldrich) was dissolved in 20 ml of 1-PrOH along with 1.32 g of acetyl acetone (99% Sigma Aldrich) and allowed to mix for 30 min prior to the introduction of 10 g of silica from Example 1. This resulted in a 98% Hf usage efficiency.

Example 17 (7.8 wt % Hf, Monomeric Hf on Q10)

A support modification as described in Example 5 was performed except that 2.00 g of Hf(iOPr)$_4$ was dissolved in 20 ml of toluene along with 1.93 g of acetyl acetone and allowed to mix for 30 min prior to the introduction of 10 g of silica from Example 1. This resulted in a 100% Hf usage efficiency.

Example 18 (11.8 wt % Hf, Trimeric Hf on Q10) (Comparative)

A support modification as described in Example 5 was performed except that 3.19 g of Hf(iOPr)$_4$ was dissolved in 20 ml of toluene instead of 1-PrOH. This resulted in a 100% Hf usage efficiency.

HRTEM Analysis of Modified Supports

Example 19 (HRTEM Analysis of Monomeric Zr)

High-Resolution Transmission Electron Microscopy (HRTEM) analysis was performed on selected modified silica examples. For this, the modified silica was flaked into particles of 100-200 nm thickness using a microtome. These flaked particles where then mounted onto a copper mesh and an antistatic osmium vapour coating was applied. The mounted sample was then analysed using a Tecnai G2 F20 (manufactured by FEI) in transmission mode. The electron beam was set at an acceleration voltage between 100 and 300 kV with a spacing resolution of 1 nm. The electron beam was focussed by a 30 μm diaphragm. HRTEM images were recorded so as to include 50-200 metal nanoparticles in an image at a magnification of 25 million times. This analysis was performed on modified silica Example 5, Example 7, Example 14, Example 15, Example 17 and Example 18. The HRTEM images are shown in FIGS. 1-6.

Cs Modification of Modified Supports

Example 20 (3.2 wt % Cs, 0.9 wt % Zr, Monomeric Zr)

0.458 g of CsOH.H$_2$O (99.5% Sigma Aldrich) was weighed out in a glovebox and dissolved in 20 ml of a 9:1 v/v MeOH:H$_2$O solvent mixture. 10 g of the modified silica from Example 3 was added to the CsOH solution with agitation. Agitation was continued for an additional 15 min after which the sample was left for 16 hours in a sealed flask with periodic agitation. After this time the extra-porous solution was removed by filtration. This was followed by a drying step where the intra-porous solvent was removed by passing a flow of nitrogen gas over the wet Cs/Zr-modified silica at room temperature. Alternatively, the intra-porous solvent was removed on a rotary evaporator at reduced pressure. Following this step, the catalyst beads were placed into a drying oven at 110-120° C. and left to dry for 16 hours. Upon cooling this yielded the Cs/Zr/SiO$_2$ catalyst with a 90% Cs usage efficiency. The Cs load (wt %) on the catalyst was determined via powder Energy Dispersive X-Ray Fluorescence analysis (Oxford Instruments X-Supreme8000).

Example 21 (3.7 wt % Cs, 0.9 wt % Zr, Monomeric Zr)

A catalyst was prepared as described in Example 20 except that 0.534 g of CsOH.H$_2$O was used.

Example 22 (4.0 wt % Cs, 0.9 wt % Zr, Monomeric Zr)

A catalyst was prepared as described in Example 20 except that 0.588 g of CsOH.H$_2$O was used.

Example 23 (4.8 wt % Cs, 0.9 wt % Zr, Monomeric Zr)

A catalyst was prepared as described in Example 20 except that 0.716 g of CsOH.H$_2$O was used.

Example 24 (5.1 wt % Cs, 1.5 wt % Zr, Monomeric Zr)

A catalyst was prepared as described in Example 20 except that 0.754 g of CsOH.H$_2$O was used and modified silica from Example 4 was used.

Example 25 (5.7 wt % Cs, 1.5 wt % Zr, Monomeric Zr)

A catalyst was prepared as described in Example 24 except that 0.852 g of CsOH.H$_2$O was used.

Example 26 (6.7 wt % Cs, 1.4 wt % Zr, Monomeric Zr)

A catalyst was prepared as described in Example 24 except that 1.00 g of CsOH.H$_2$O was used.

Example 27 (7.7 wt % Cs, 1.4 wt % Zr, Monomeric Zr)

A catalyst was prepared as described in Example 24 except that 1.17 g of CsOH.H$_2$O was used.

Example 28 (9.7 wt % Cs, 2.0 wt % Zr, Monomeric Zr)

A catalyst was prepared as described in Example 20 except that 1.37 g of CsOH.H$_2$O was used and modified silica from Example 5 was used. Additionally, the Cs adsorption time was shortened from 16 hours to 2 hours with the filtration step being excluded. The excess organic solvent was dried into the pore volume of the modified silica support and resulted in a Cs usage efficiency of 100%.

Example 29 (10.2 wt % Cs, 2.0 wt % Zr, Monomeric Zr)

A catalyst was prepared as described in Example 28 except that 1.45 g of CsOH.H$_2$O was used.

Example 30 (10.8 wt % Cs, 2.0 wt % Zr, Monomeric Zr)

A catalyst was prepared as described in Example 28 except that 1.54 g of CsOH.H$_2$O was used.

Example 31 (11.3 wt % Cs, 2.0 wt % Zr, Monomeric Zr)

A catalyst was prepared as described in Example 28 except that 1.62 g of CsOH.H$_2$O was used.

Example 32 (9.2 wt % Cs, 2.4 wt % Zr, Monomeric Zr)

A catalyst was prepared as described in Example 20 except that 1.44 g of CsOH.H$_2$O was used and modified silica from Example 6 was used.

Example 33 (10.9 wt % Cs, 2.4 wt % Zr, Monomeric Zr)

A catalyst was prepared as described in Example 32 except that 1.74 g of CsOH.H$_2$O was used.

Example 34 (13.0 wt % Cs, 2.3 wt % Zr, Monomeric Zr)

A catalyst was prepared as described in Example 32 except that 2.12 g of CsOH.H$_2$O was used.

Example 35 (14.0 wt % Cs, 2.3 wt % Zr, Monomeric Zr)

A catalyst was prepared as described in Example 32 except that 2.30 g of CsOH.H$_2$O was used.

Example 36 (12.3 wt % Cs, 3.7 wt % Zr, Monomeric Zr)

A catalyst was prepared as described in Example 20 except that 2.00 g of CsOH.H$_2$O was used and modified silica from Example 7 was used.

Example 37 (12.6 wt % Cs, 3.7 wt % Zr, Monomeric Zr)

A catalyst was prepared as described in Example 36 except that 2.05 g of CsOH.H$_2$O was used.

Example 38 (13.9 wt % Cs, 3.6 wt % Zr, Monomeric Zr)

A catalyst was prepared as described in Example 36 except that 2.30 g of CsOH.H$_2$O was used.

Example 39 (15.4 wt % Cs, 3.6 wt % Zr, Monomeric Zr)

A catalyst was prepared as described in Example 36 except that 2.60 g of CsOH.H$_2$O was used.

Example 40 (2.8 wt % Cs, 0.7 wt % Zr, Monomeric Zr)

A catalyst was prepared as described in Example 28 except that 0.37 g of CsOH.H$_2$O was used and modified silica from Example 8 was used.

Example 41 (3.4 wt % Cs, 0.7 wt % Zr, Monomeric Zr)

A catalyst was prepared as described in Example 40 except that 0.45 g of CsOH.H$_2$O was used.

Example 42 (3.9 wt % Cs, 0.7 wt % Zr, Monomeric Zr)

A catalyst was prepared as described in Example 40 except that 0.51 g of CsOH.H$_2$O was used.

Example 43 (4.1 wt % Cs, 1.0 wt % Zr, Monomeric Zr)

A catalyst was prepared as described in Example 20 except that 0.60 g of CsOH.H$_2$O was used and modified silica from Example 9 was used.

Example 44 (4.6 wt % Cs, 1.0 wt % Zr, Monomeric Zr)

A catalyst was prepared as described in Example 43 except that 0.68 g of CsOH.H$_2$O was used.

Example 45 (5.5 wt % Cs, 1.0 wt % Zr, Monomeric Zr)

A catalyst was prepared as described in Example 43 except that 0.82 g of CsOH.H$_2$O was used.

Example 46 (9.1 wt % Cs, 2.0 wt % Zr, Monomeric Zr)

A catalyst was prepared as described in Example 20 except that 1.42 g of $CsOH \cdot H_2O$ was used and modified silica from Example 10 was used.

Example 47 (9.9 wt % Cs, 1.9 wt % Zr, Monomeric Zr)

A catalyst was prepared as described in Example 46 except that 1.55 g of $CsOH \cdot H_2O$ was used.

Example 48 (13.8 wt % Cs, 3.3 wt % Zr, Monomeric Zr)

A catalyst was prepared as described in Example 20 except that 2.28 g of $CsOH \cdot H_2O$ was used and modified silica from Example 11 was used.

Example 49 (15.0 wt % Cs, 3.3 wt % Zr, Monomeric Zr)

A catalyst was prepared as described in Example 48 except that 2.51 g of $CsOH \cdot H_2O$ was used.

Example 50 (14.0 wt % Cs, 5.7 wt % Zr, Dimeric Zr) (Comparative)

A catalyst was prepared as described in Example 20 except that 2.34 g of $CsOH \cdot H_2O$ was used and modified silica from Example 12 was used.

Example 51 (15.0 wt % Cs, 5.7 wt % Zr, Dimeric Zr) (Comparative)

A catalyst was prepared as described in Example 50 except that 2.54 g of $CsOH \cdot H_2O$ was used.

Example 52 (16.1 wt % Cs, 5.6 wt % Zr, Dimeric Zr) (Comparative)

A catalyst was prepared as described in Example 50 except that 2.76 g of $CsOH \cdot H_2O$ was used.

Example 53 (17.3 wt % Cs, 5.5 wt % Zr, Dimeric Zr) (Comparative)

A catalyst was prepared as described in Example 50 except that 3.01 g of $CsOH \cdot H_2O$ was used.

Example 54 (6.0 wt % Cs, 2.1 wt % Zr, Trimeric Zr) (Comparative)

A catalyst was prepared as described in Example 28 except that 0.81 g of $CsOH \cdot H_2O$ was used and modified silica from Example 13 was used.

Example 55 (7.7 wt % Cs, 2.0 wt % Zr, Trimeric Zr) (Comparative)

A catalyst was prepared as described in Example 54 except that 1.06 g of $CsOH \cdot H_2O$ was used.

Example 56 (13.6 wt % Cs, 5.2 wt % Zr, Trimeric Zr) (Comparative)

A catalyst was prepared as described in Example 28 except that 2.03 g of $CsOH \cdot H_2O$ was used and modified silica from Example 14 was used.

Example 57 (14.9 wt % Cs, 5.1 wt % Zr, Trimeric Zr) (Comparative)

A catalyst was prepared as described in Example 56 except that 2.26 g of $CsOH \cdot H_2O$ was used.

Example 58 (16.1 wt % Cs, 5.0 wt % Zr, Trimeric Zr) (Comparative)

A catalyst was prepared as described in Example 56 except that 2.48 g of $CsOH \cdot H_2O$ was used.

Example 59 (17.3 wt % Cs, 5.0 wt % Zr, Trimeric Zr) (Comparative)

A catalyst was prepared as described in Example 56 except that 2.70 g of $CsOH \cdot H_2O$ was used.

Example 60 (12.3 wt % Cs, 7.0 wt % Zr, Pentameric Zr) (Comparative)

A catalyst was prepared as described in Example 28 except that 1.82 g of $CsOH \cdot H_2O$ was used and modified silica from Example 15 was used.

Example 61 (14.0 wt % Cs, 6.9 wt % Zr, Pentameric Zr) (Comparative)

A catalyst was prepared as described in Example 60 except that 2.12 g of $CsOH \cdot H_2O$ was used.

Example 62 (15.7 wt % Cs, 6.7 wt % Zr, Pentameric Zr) (Comparative)

A catalyst was prepared as described in Example 60 except that 2.42 g of $CsOH \cdot H_2O$ was used.

Example 63 (18.9 wt % Cs, 6.5 wt % Zr, Pentameric Zr) (Comparative)

A catalyst was prepared as described in Example 60 except that 2.99 g of $CsOH \cdot H_2O$ was used.

Example 64 (8.8 wt % Cs, 4.9 wt % Hf, Monomeric Hf)

A catalyst was prepared as described in Example 28 except that 1.23 g of $CsOH \cdot H_2O$ was used and modified silica from Example 16 was used.

Example 65 (10.1 wt % Cs, 4.9 wt % Hf, Monomeric Hf)

A catalyst was prepared as described in Example 64 except that 1.43 g of $CsOH \cdot H_2O$ was used.

Example 66 (11.4 wt % Cs, 4.8 wt % Hf, Monomeric Hf)

A catalyst was prepared as described in Example 64 except that 1.64 g of $CsOH \cdot H_2O$ was used.

Example 67 (12.6 wt % Cs, 4.7 wt % Hf, Monomeric Hf)

A catalyst was prepared as described in Example 64 except that 1.84 g of CsOH.H$_2$O was used.

Example 68 (11.1 wt % Cs, 6.9 wt % Hf, Monomeric Hf)

A catalyst was prepared as described in Example 28 except that 1.60 g of CsOH.H$_2$O was used and modified silica from Example 17 was used.

Example 69 (12.7 wt % Cs, 6.8 wt % Hf, Monomeric Hf)

A catalyst was prepared as described in Example 68 except that 1.86 g of CsOH.H$_2$O was used.

Example 70 (14.3 wt % Cs, 6.7 wt 5 Hf, Monomeric Hf)

A catalyst was prepared as described in Example 68 except that 2.14 g of CsOH.H$_2$O was used.

Example 71 (15.8 wt % Cs, 6.6 wt % Hf, Monomeric Hf)

A catalyst was prepared as described in Example 68 except that 2.41 g of CsOH.H$_2$O was used.

Example 72 (13.7 wt % Cs, 10.2 wt % Hf, Trimeric Hf) (Comparative)

A catalyst was prepared as described in Example 20 except that 2.28 g of CsOH.H$_2$O was used and modified silica from Example 18 was used.

Example 73 (14.9 wt % Cs, 10.0 wt % Hf, Trimeric Hf) (Comparative)

A catalyst was prepared as described in Example 72 except that 2.51 g of CsOH.H$_2$O was used.

Example 74 (16.2 wt % Cs, 9.9 wt % Hf, Trimeric Hf) (Comparative)

A catalyst was prepared as described in Example 72 except that 2.77 g of CsOH.H$_2$O was used.

Example 75 (16.0 wt % Cs, 3.4 wt % Zr, 100% Monomeric Zr)

A catalyst was prepared as described in Example 20 except that 2.71 g of CsOH.H$_2$O was used and 10 g of modified silica from Example 7 was used. Additionally, after the catalyst had been dried it was crushed using a mortar and pestle and sieved into a 0.1-1.0 mm size fraction. This resulted in a catalyst with a 100% monomeric content based on wt % Zr basis.

Example 76 (15.8 Wt % Cs, 3.6 wt % Zr, 79% Monomeric Zr) (Comparative)

A catalyst was prepared as described in Example 75 except that 2.67 g of CsOH.H$_2$O was used. Additionally 8.5 g of modified silica from Example 7 and 1.5 g of modified silica from Example 14 were used as catalyst support. This resulted in a catalyst with a 79% monomeric content based on wt % Zr basis.

Example 77 (15.4 wt % Cs, 3.9 wt % Zr, 61% Monomeric Zr) (Comparative)

A catalyst was prepared as described in Example 75 except that 2.60 g of CsOH.H$_2$O was used. Additionally 7 g of modified silica from Example 7 and 3 g of modified silica from Example 14 were used as catalyst support. This resulted in a catalyst with a 61% monomeric content based on wt % Zr basis.

Example 78 (15.7 wt % Cs, 4.4 wt % Zr, 31% Monomeric Zr) (Comparative)

A catalyst was prepared as described in Example 75 except that 2.66 g of CsOH.H$_2$O was used. Additionally, 4 g of modified silica from Example 7 and 6 g of modified silica from Example 14 were used as catalyst support. This resulted in a catalyst with a 31% monomeric content based on wt % Zr basis.

Example 79 (16.9 wt % Cs, 5.0 wt % Zr, 0% Monomeric Zr) (Comparative)

A catalyst was prepared as described in Example 75 except that 2.92 g of CsOH.H$_2$O was used. Additionally, 10 g of modified silica from Example 14 were used as catalyst support. This resulted in a catalyst with a 0% monomeric content based on wt % Zr basis.

Example 80 (Catalytic Performance Testing)

Catalysts from Example 20 to Example 79 were tested for the reaction of methyl propionate and formaldehyde in a labscale microreactor. For this, 3 g of catalyst was loaded into a fixed bed reactor with an internal tube diameter of 10 mm. The reactor was heated to 330° C. and preconditioning was performed by feeding a vaporised stream comprising of 70 wt % methyl propionate, 20 wt % methanol, 6 wt % water and 4 wt % formaldehyde from a vaporiser fed by a Gilson pump at 0.032 ml/min. This preconditioning was continued overnight. After preconditioning a feed stream comprising of 75.6 wt % methyl propionate, 18.1 wt % methanol, 5.7 wt % formaldehyde and 0.6 wt % water, was pumped by a Gilson pump to a vaporiser set at 330° C. before being fed to the heated reactor set at 330° C. containing the catalyst. The reactor exit vapour was cooled and condensed with samples being collected at five different liquid feed rates (between 0.64-0.032 ml/min) so as to obtain conversions at varying vapour/catalyst contact times. The liquid feed and condensed ex-reactor liquid products were analysed by a Shimadzu 2010 Gas Chromatograph with a DB1701 column. The compositions of the samples were determined from the respective chromatograms and yields and selectivities at varying contact times determined. Activity was defined as the inverse of the contact time, in seconds, required to obtain 10% MMA+MAA yield on methyl propionate fed and was determined via an interpolation on a contact time vs. MMA+MAA yield graph. This interpolated contact time was then used to obtain the MMA+MAA selectivity at 10% MMA+MAA yield.

TABLE 1

Activity and MMA + MAA selectivity results for catalyst prepared on the Zr modified support examples with varying Zr nuclearity.

| Example | Zirconium nuclearity | Zr load (wt %) | Cs load (wt %) | Cs:Zr (molar ratio) | Activity at 10% MMA + MAA yield (1/s) | MMA + MAA selectivity (%) |
|---|---|---|---|---|---|---|
| Example 20 | 1 | 0.9 | 3.2 | 2.4 | 0.12 | 95.8 |
| Example 21 | 1 | 0.9 | 3.7 | 2.8 | 0.15 | 97.3 |
| Example 22 | 1 | 0.9 | 4.0 | 3.1 | 0.18 | 97.6 |
| Example 23 | 1 | 0.9 | 4.8 | 3.8 | 0.24 | 98.0 |
| Example 24 | 1 | 1.5 | 5.1 | 2.4 | 0.32 | 97.4 |
| Example 25 | 1 | 1.5 | 5.7 | 2.7 | 0.39 | 97.1 |
| Example 26 | 1 | 1.4 | 6.7 | 3.2 | 0.41 | 97.0 |
| Example 27 | 1 | 1.4 | 7.7 | 3.7 | 0.47 | 97.3 |
| Example 28 | 1 | 2.0 | 9.7 | 3.3 | 0.45 | 96.1 |
| Example 29 | 1 | 2.0 | 10.2 | 3.5 | 0.39 | 95.8 |
| Example 30 | 1 | 2.0 | 10.8 | 3.7 | 0.49 | 95.8 |
| Example 31 | 1 | 2.0 | 11.3 | 3.9 | 0.46 | 95.5 |
| Example 32 | 1 | 2.4 | 9.2 | 2.6 | 0.48 | 96.8 |
| Example 33 | 1 | 2.4 | 10.9 | 3.2 | 0.64 | 96.2 |
| Example 34 | 1 | 2.3 | 13.0 | 3.9 | 0.67 | 95.5 |
| Example 35 | 1 | 2.3 | 14.0 | 4.2 | 0.75 | 95.5 |
| Example 36 | 1 | 3.7 | 12.3 | 2.3 | 0.76 | 95.3 |
| Example 37 | 1 | 3.7 | 12.6 | 2.4 | 0.80 | 95.0 |
| Example 38 | 1 | 3.6 | 13.9 | 2.7 | 0.86 | 94.1 |
| Example 39 | 1 | 3.6 | 15.4 | 3.0 | 0.93 | 94.5 |
| Example 40 | 1 | 0.7 | 2.8 | 2.7 | 0.13 | 97.5 |
| Example 41 | 1 | 0.7 | 3.4 | 3.3 | 0.17 | 97.9 |
| Example 42 | 1 | 0.7 | 3.9 | 3.8 | 0.25 | 97.8 |
| Example 43 | 1 | 1.0 | 4.1 | 2.7 | 0.25 | 96.3 |
| Example 44 | 1 | 1.0 | 4.6 | 3.1 | 0.28 | 97.8 |
| Example 45 | 1 | 1.0 | 5.5 | 3.7 | 0.35 | 96.7 |
| Example 46 | 1 | 2.0 | 9.1 | 3.2 | 0.47 | 96.5 |
| Example 47 | 1 | 1.9 | 9.9 | 3.5 | 0.71 | 96.5 |
| Example 48 | 1 | 3.3 | 13.8 | 2.9 | 0.75 | 94.5 |
| Example 49 | 1 | 3.3 | 15.0 | 3.2 | 0.76 | 94.8 |
| Example 50 | 2 | 5.7 | 14.0 | 1.7 | 0.69 | 93.0 |
| Example 51 | 2 | 5.7 | 15.0 | 1.8 | 0.82 | 93.0 |
| Example 52 | 2 | 5.6 | 16.1 | 2.0 | 0.85 | 93.2 |
| Example 53 | 2 | 5.5 | 17.3 | 2.2 | 0.68 | 92.0 |
| Example 54 | 3 | 2.1 | 6.0 | 2.0 | 0.26 | 89.2 |
| Example 55 | 3 | 2.0 | 7.7 | 2.5 | 0.34 | 88.8 |
| Example 56 | 3 | 5.2 | 13.6 | 1.8 | 0.38 | 85.7 |
| Example 57 | 3 | 5.1 | 14.9 | 2.0 | 0.47 | 88.7 |
| Example 58 | 3 | 5.0 | 16.1 | 2.2 | 0.51 | 90.7 |
| Example 59 | 3 | 5.0 | 17.3 | 2.4 | 0.41 | 90.2 |
| Example 60 | 5 | 7.0 | 12.3 | 1.2 | 0.24 | 76.0 |
| Example 61 | 5 | 6.9 | 14.0 | 1.4 | 0.45 | 85.0 |
| Example 62 | 5 | 6.7 | 15.7 | 1.6 | 0.56 | 87.0 |
| Example 63 | 5 | 6.5 | 18.9 | 2.0 | 0.85 | 87.6 |

TABLE 2

Activity and MMA + MAA selectivity results for catalyst prepared on the Hf modified support examples with varying Hf nuclearity.

| Example | Hafnium nuclearity | Hf load (wt %) | Cs load (wt %) | Cs:Hf (molar ratio) | Activity at 10% MMA + MAA yield (1/s) | MMA + MAA selectivity (%) |
|---|---|---|---|---|---|---|
| Example 64 | 1 | 4.9 | 8.8 | 2.4 | 0.51 | 97.2 |
| Example 65 | 1 | 4.9 | 10.1 | 2.8 | 0.58 | 97.1 |
| Example 66 | 1 | 4.8 | 11.4 | 3.2 | 0.64 | 96.5 |
| Example 67 | 1 | 4.7 | 12.6 | 3.6 | 0.73 | 96.5 |
| Example 68 | 1 | 6.9 | 11.1 | 2.2 | 0.68 | 96.4 |
| Example 69 | 1 | 6.8 | 12.7 | 2.5 | 0.82 | 96.5 |
| Example 70 | 1 | 6.7 | 14.3 | 2.9 | 0.88 | 96.0 |
| Example 71 | 1 | 6.6 | 15.8 | 3.2 | 0.88 | 95.1 |
| Example 72 | 3 | 10.2 | 13.7 | 1.8 | 0.58 | 89.8 |
| Example 73 | 3 | 10.0 | 14.9 | 2.0 | 0.71 | 91.6 |
| Example 74 | 3 | 9.9 | 16.2 | 2.2 | 0.69 | 91.2 |

TABLE 3

Activity and MMA + MAA selectivity results for catalyst prepared with varying amounts of Zr monomer and trimer.

| Example | Monomeric Zr content (% of Zr content) | Zr load (wt %) | Cs load (wt %) | Cs:Zr (molar ratio) | Activity at 10% MMA + MAA yield (1/s) | MMA + MAA selectivity (%) |
|---|---|---|---|---|---|---|
| Example 75 | 100 | 3.4 | 16.0 | 3.3 | 1.43 | 95.8 |
| Example 76 | 79 | 3.6 | 15.8 | 3.0 | 1.44 | 94.9 |
| Example 77 | 61 | 3.9 | 15.4 | 2.7 | 1.40 | 93.7 |
| Example 78 | 31 | 4.4 | 15.7 | 2.5 | 1.31 | 92.0 |
| Example 79 | 0 | 5.0 | 16.9 | 2.4 | 1.29 | 88.6 |

Example 81 (Accelerated Ageing Tests)

Catalyst sintering resistance was assessed in an accelerated ageing test. For this, 1 g of catalyst was loaded into a U-tube stainless steel reactor and loaded into an oven. The oven was heated to 385° C. and a stream of nitrogen (10 ml/min) was passed through a saturating vaporiser containing water that was heated to 92° C. This ensured that a feed stream with a water partial pressure of 0.75 bara was passed over the catalyst heated to 385° C. Periodically the surface area of the catalyst samples was determined ex-situ using nitrogen adsorption/desorption isotherm analysis (Micromeretics Tristar II). The measured surface area values were used to determine sintering rates constants for each catalyst and is described as $g^3 \cdot m^{-6} \cdot d^{-1}$. The higher the sintering constant, the lower the sintering resistance of the catalyst. This test was performed on Example 32, Example 38, Example 57 and Example 63.

TABLE 4

Accelerating ageing data for the catalysts of varying Zr nuclearity with comparable activity.

| | Surface area at time (days) | | | | | Catalyst activity (1/s) | Sintering rate constant ($g^3 \cdot m^{-6} \cdot d^{-1}$) |
|---|---|---|---|---|---|---|---|
| Example | 1 | 7 | 14 | 21 | 28 | | |
| Example 32 (inventive) | 189 | 187 | 177 | 176 | 178 | 0.48 | 1.28E-09 |
| Example 38 (inventive) | 163 | 147 | 144 | 135 | 135 | 0.86 | 6.35E-09 |
| Example 57 (comparative) | 218 | 209 | 192 | 192 | 185 | 0.47 | 2.26E-09 |
| Example 63 (comparative) | 148 | 132 | 124 | 127 | 119 | 0.85 | 8.94E-09 |

Comparative Examples 82 and 83

Examples were prepared according to experimental examples disclosed in EP 1233330. In these examples the silica employed was a gel silica in the form of spheres of diameter in the range 2-4 mm having a purity of over 99%, a total surface area of about 300-350 m²/g, and a pore volume of 1.04 cm³/g with 76% of the pore volume provided by pores having a diameter in the range 7-23 nm.

Two catalysts were prepared by impregnating the silica with an aqueous solution of zirconium nitrate, sufficient to fill the pores of the support, and drying in a rotary evaporator and then in an air oven at 120° C. for 2 hours. In one case (example 82), the impregnation of the zirconium solution was assisted by evacuation of the pores of the support prior to addition of the solution. In the other case (example 83), impregnation of the zirconium solution was carried out in an atmospheric pressure of air. Caesium was then incorporated by a similar procedure using an aqueous solution of caesium carbonate, to give a caesium content of 4% by weight (expressed as metal). The catalysts were then calcined in air at 450° C. for 3 hours.

Catalysts were tested under the same conditions as described in example 80. One catalyst (example 82) failed to achieve 10% yield and selectivities are shown for the highest obtained yield (9.6%).

TABLE 5

Activity and MMA + MAA selectivity results for comparative examples 82 and 83.

| Example | Zr load (wt %) | Cs load (wt %) | Cs:Zr (molar ratio) | Activity at 10% MMA + MAA yield (1/s) | MMA + MAA selectivity (%) |
|---|---|---|---|---|---|
| Example 82 | 1.7 | 4.0 | 1.6 | 0.05 | 65.2 |
| Example 83 | 1.7 | 4.0 | 1.6 | 0.12 | 73.2 |

HRTEM Results for Zr and Hf Modified Silica Supports

The HRTEM images (Example 19) for the Zr and Hf modified silica examples (Example 5, Example 7, Example 14, Example 15, Example 17 and Example 18) are shown in FIG. 1 to FIG. 6. In the case of the HRTEM images of monomeric Zr and Hf, it is difficult to distinguish clear Zr or Hf particles and this is indicative of very small Zr/Hf nanoparticles present on the modified silica surface. This is due to the Zr or Hf being present as monoatomic atoms. In the case of the trimeric Zr or Hf and pentameric Zr examples, clear Zr or Hf clusters can be distinguished on the modified support HRTEM images. This data shows that the solution phase nuclearity of the Zr or Hf species is transferred from solution to final catalyst formulation.

Graphed Data

Activity and Selectivity Data Constructed from Table 1 and Table 2

The MMA+MAA selectivity (%) vs. catalyst activity for the catalysts prepared in Example 20 to Example 74 is shown in FIG. 7. From this graph it is clear that the trimeric Zr and Hf as well as pentameric Zr results in lower MMA+MAA selectivity across the entire activity range examined. The dimeric Zr catalyst show improved selectivity compared to the trimeric Zr catalysts at comparable Zr and Cs loadings.

Activity and Selectivity Data Constructed from Table 3

The catalyst selectivity for mixed monomer/trimer catalysts prepared in Example 75 to Example 79 is shown in FIG. 8. The Zr monomer is content is calculated as the % of Zr content present as monomer. In these examples the catalyst was crushed and sieved to 0.1-1.0 mm particles in order to increase sample homogeneity. From this graph it is clear that decreasing amounts of Zr monomer in the formulation will result in a decreasing MMA+MAA selectivity.

Sintering Resistance Data Constructed from Table 4

The catalyst sintering constants as determined by the advanced ageing test described in Example 81 is shown in FIG. 9. From FIG. 9 it is clear that monomeric Zr catalysts display lower sintering rates at comparable catalyst activity.

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the preferred, typical or optional invention features disclosed in this specification (including any accompanying claims, abstract or drawings), or to any novel one, or any novel combination, of the preferred, typical or optional invention steps of any method or process so disclosed.

The invention claimed is:

1. A catalyst comprising
   a) a silica support modified with a modifier metal present on a surface thereof, and
   b) a catalytic metal on the silica support,
   wherein the modifier metal is selected from the group consisting of zirconium and hafnium with at least a proportion of the modifier metal present as a monomeric and/or dimeric metal moiety, wherein the catalytic metal is at least one alkali metal.

2. A catalyst according to claim 1, wherein the modifier metal is present in the silica support in an effective amount to reduce sintering and improve selectivity of the catalyst.

3. A catalyst according to claim 1, wherein the catalytic metal is caesium.

4. A catalyst according to claim 1, wherein catalytic metal is present in the range 0.5-7.0 mol/mol modifier metal.

5. A modified silica support for a catalyst having at least one alkali metal comprising a silica support modified with a modifier metal present on a surface thereof, wherein the modifier metal is selected from the group consisting of zirconium and/or hafnium with at least a proportion of the modifier metal present as a monomeric and/or dimeric metal oxide moiety.

6. A modified silica support according to claim 5, wherein the modifier metal is an adsorbate adsorbed on the silica support surface.

7. A modified silica support according to claim 5, wherein the silica support is in the form of a silica gel.

8. A modified silica support according to claim 5, wherein the modifier metal is present in the support in the form of a co-gel.

9. A modified silica support according to claim 5, wherein at least 25% of the modifier metal in the modified silica support is present as the monomeric and/or dimeric metal oxide moiety.

10. A modified silica support according to claim 5, wherein the level of modifier metal present is up to $7.6 \times 10^{-2}$ mol/mol of silica.

11. A modified silica support according to claim 5, wherein the level of modifier metal is between $0.067 \times 10^{-2}$ and $7.3 \times 10^{-2}$ mol/mol of silica.

12. A modified silica support according to claim 5, wherein the level of modifier metal present is at least $0.1 \times 10^{-2}$ mol/mol of silica.

13. A modified silica support according to claim 5, wherein the modified silica support is a calcined modified silica support.

* * * * *